US011543157B2

United States Patent
Lee et al.

(10) Patent No.: US 11,543,157 B2
(45) Date of Patent: Jan. 3, 2023

(54) RADIATIVE COOLING DEVICE AND METHOD OF MANUFACTURING THE SAME

(71) Applicant: Korea University Research and Business Foundation, Seoul (KR)

(72) Inventors: Heon Lee, Seoul (KR); Pil-Hoon Jung, Yongin-si (KR); Soomin Son, Seoul (KR); Dongwoo Chae, Seoul (KR); Yuting Liu, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 102 days.

(21) Appl. No.: 15/734,643

(22) PCT Filed: Oct. 14, 2020

(86) PCT No.: PCT/KR2020/014010
§ 371 (c)(1),
(2) Date: Dec. 3, 2020

(87) PCT Pub. No.: WO2021/085895
PCT Pub. Date: May 6, 2021

(65) Prior Publication Data
US 2021/0310700 A1     Oct. 7, 2021

(30) Foreign Application Priority Data

Oct. 31, 2019   (KR) .......................... 10-2019-0137538
Nov. 22, 2019   (KR) .......................... 10-2019-0151729

(51) Int. Cl.
*F24S 70/25*     (2018.01)
*F24S 50/80*     (2018.01)
(Continued)

(52) U.S. Cl.
CPC ............... *F24S 70/25* (2018.05); *F24S 50/80* (2018.05); *F24S 70/225* (2018.05); *F24S 2070/62* (2018.05)

(58) Field of Classification Search
CPC .......... F24S 70/25; F24S 70/225; F24S 70/62; F24S 50/80; G02B 17/06; G02B 17/00; G02B 5/26; G02B 5/22
(Continued)

(56) References Cited

U.S. PATENT DOCUMENTS 5,239,406 A * 8/1993 Lynam .............. B32B 17/10339
                                                        359/275
5,339,198 A * 8/1994 Wheatly ................ G02B 5/287
                                                        359/359
(Continued)

FOREIGN PATENT DOCUMENTS

AU     2010202064 A1 * 12/2010  ........... C23C 28/322
CN     107923718 A      4/2018
(Continued)

OTHER PUBLICATIONS

"CN_110567188_A_I—Machine Translation.pdf", Machine Translation, Clarivate Analytics, May 10, 2022. (Year: 2022).*
(Continued)

*Primary Examiner* — Steven B McAllister
*Assistant Examiner* — Daniel E. Namay
(74) *Attorney, Agent, or Firm* — NSIP Law

(57) ABSTRACT

A radiative cooling device, and a method of manufacturing the same, includes a reflective layer disposed on a substrate and responsible for reflecting sunlight having wavelengths corresponding to ultraviolet, visible, and near-infrared regions; and a radiative cooling layer disposed on the reflective layer and responsible for absorbing sunlight having a wavelength corresponding to a mid-infrared region and
(Continued)

emitting the sunlight as heat, wherein the radiative cooling layer includes a first radiation layer including an uneven pattern; and a second radiation layer disposed on the first radiation layer and having a refractive index different from that of the first radiation layer.

19 Claims, 22 Drawing Sheets

(51) Int. Cl.
*F24S 70/225* (2018.01)
*F24S 70/60* (2018.01)

(58) Field of Classification Search
USPC ................ 126/684, 92 B, 92 S, 92 AC, 91; 431/326–329, 100; 359/360, 359, 361
See application file for complete search history.

(56) References Cited

U.S. PATENT DOCUMENTS

| | | | |
|---|---|---|---|
| 5,540,978 A * | 7/1996 | Schrenk | G02B 5/305 |
| | | | 428/339 |
| 5,552,927 A * | 9/1996 | Wheatly | G02B 5/26 |
| | | | 359/359 |
| 7,378,655 B2 * | 5/2008 | Tai | G01J 3/26 |
| | | | 250/338.1 |
| 9,927,188 B2 | 3/2018 | Liu et al. | |
| 10,088,251 B2 | 10/2018 | Raman et al. | |
| 10,094,163 B2 * | 10/2018 | Hartig | C03C 17/36 |
| 10,126,020 B2 * | 11/2018 | Villuendas | F24S 70/25 |
| 10,184,052 B2 * | 1/2019 | Hitomi | G02B 5/22 |
| 10,351,717 B2 * | 7/2019 | Abendroth | C23C 16/407 |
| 10,533,777 B2 * | 1/2020 | Ren | G02B 1/115 |
| 10,774,426 B2 * | 9/2020 | Kuckelkorn | C23C 28/36 |
| 11,360,248 B2 * | 6/2022 | Sharma | G02B 5/0294 |
| 11,360,251 B2 * | 6/2022 | Arike | G02B 5/208 |
| 11,391,872 B2 * | 7/2022 | Leturcq | C23C 16/45525 |
| 2004/0089807 A1 * | 5/2004 | Wada | G01J 5/20 |
| | | | 250/338.1 |
| 2015/0338175 A1 * | 11/2015 | Raman | F24F 5/0089 |
| | | | 165/185 |
| 2015/0338675 A1 * | 11/2015 | Zhang | G02F 1/133516 |
| | | | 156/60 |
| 2019/0040520 A1 * | 2/2019 | Krammer | F24S 70/30 |

FOREIGN PATENT DOCUMENTS

| | | | |
|---|---|---|---|
| CN | 108699363 A | | 10/2018 |
| CN | 110274326 A | | 9/2019 |
| CN | 110567188 A | | 12/2019 |
| CN | 111155332 A | | 5/2020 |
| JP | 2006-340675 A | | 12/2006 |
| JP | 2008-281906 A | | 11/2008 |
| JP | 2010-460 A | | 1/2010 |
| JP | 2010-251432 A | | 11/2010 |
| JP | 2011-212849 A | | 10/2011 |
| JP | 2016-133520 A | | 7/2016 |
| KR | 10-2015-0018694 A | | 2/2015 |
| KR | 10-2016-0147650 A | | 12/2016 |
| KR | 10-2019-0101870 A | | 9/2019 |
| KR | 10-2036071 B1 | | 10/2019 |
| TW | 200809133 A | | 2/2008 |
| WO | WO 2013/179902 A1 | | 12/2013 |
| WO | WO 2016/208514 A1 | | 12/2016 |
| WO | WO 2020/195743 A1 | | 10/2020 |

OTHER PUBLICATIONS

Extended European Search Report dated May 12, 2021 in counterpart European Patent Application No. 20211867.5 (10 pages in English).
Korean Office Action dated Oct. 20, 2020 in counterpart Korean Patent Application No. 10-2019-0137538 ( 6 pages in Korean).
Korean Office Action dated Oct. 27, 2020 in counterpart Korean Patent Application No. 10-2019-0151729 ( 5 pages in Korean).
Korean Notice of Allowance dated Feb. 5, 2021 in counterpart Korean Patent Application No. 10-2019-0137538 (4 pages in Korean).
Chinese Office Action dated Apr. 12, 2022 in corresponding Chinese Patent Application No. 202080003155.4 (10 pages in Chinese).

* cited by examiner

RADIATIVE COOLING DEVICE AND METHOD OF MANUFACTURING THE SAME

CROSS-REFERENCE TO RELATED APPLICATIONS

This application is a National Stage Entry of PCT International Application No. PCT/KR2020/014010, which was filed on Oct. 14, 2020, and which claims priority to Korean Patent Application No. 10-2019-0137538, filed on Oct. 31, 2019, and Korean Patent Application No. 10-2019-0151729, filed on Nov. 22, 2019, in the Korean Intellectual Property Office, the disclosures of each of which are incorporated herein by reference.

TECHNICAL FIELD

The present invention relates to a radiative cooling device and a method of manufacturing the same.

BACKGROUND ART

In general, energy consumption is required for cooling. General-purpose cooling devices such as refrigerators and air conditioners compress a refrigerant using energy and then perform cooling by absorbing heat generated when the compressed refrigerant is expanded. In contrast, radiative cooling is a technology that can cool without consuming energy.

For radiative cooling, absorption, reflection, and radiation of light in each wavelength band must be effectively controlled.

In most cases, a heat source is incident sunlight, and the heat of sunlight is distributed in wavelength ranges corresponding to UV-visible light-near infrared regions. When light corresponding to these wavelength ranges is reflected, inflow of heat through sunlight may be blocked.

When a material has a reflectance of 100% with respect to UV, visible light, and near-infrared light, this means that the material reflects 100% of the energy of incident sunlight and does not absorb the sunlight at all.

For example, the internal temperature of a black car, which absorbs a lot of light in broad daylight, increases rapidly, but in the case of a white car, which absorbs relatively little light and reflects a lot of light, the internal temperature thereof increases slowly.

When the surface of a car reflects all UV, visible light, and near-infrared light, inflow of heat energy by sunlight may be blocked.

All objects emit heat to the outside in the form of light, and the wavelength band of the emitted light is determined by the surface temperature of the objects.

Since the surface temperature of the sun is 6,000° C., the sun emits light corresponding to the UV-visible-near-infrared wavelength band to the outside.

A material having a surface temperature of several tens of degrees C. emits mid-infrared light with a wavelength of several tens of micrometers to the outside.

When radiation of mid-infrared light from the surface of a material is blocked or coating is performed using a coating material that reflects emitted light again, heat loss due to mid-infrared radiation may be reduced, and thermal insulation effect may be achieved.

Water vapor and carbon dioxide exist in the atmosphere of the earth, and these gases absorb some wavelengths of mid-infrared light emitted from the earth to the outside and suppress emission of mid-infrared light.

However, mid-infrared light of a wavelength of 8 to 13 µm, commonly referred to as atmospheric window, is not absorbed by the atmosphere of the earth, so the mid-infrared light is called as atmospheric window. Infrared light in this wavelength is not absorbed by the atmosphere and is emitted into space.

When all incident sunlight (emitted from the sun) corresponding to UV-visible light-near-infrared regions is reflected and mid-infrared light having a wavelength of 8 to 13 µm corresponding to the atmospheric window is effectively emitted to the outside, heat inflow may be blocked and heat emission may be maximized, and thus cooling of a material may be performed without energy consumption.

As a solar reflective material, a metal material that is transparent to sunlight and can effectively emit long-wavelength infrared light is mainly used. Accordingly, most radiative cooling devices have a metallic mirror-like color.

This metallic mirror-like color may be a disadvantage in the application of radiative cooling materials.

Radiative cooling devices may be used in automobiles, buildings, containers, etc. to reduce energy consumption required for cooling. However, since the color of the radiative cooling device is limited to the color of a metallic mirror. Thus, there is a demand for a radiative cooling device having various colors while having the same cooling performance.

DISCLOSURE

Technical Problem

Therefore, the present invention has been made in view of the above problems, and it is one object of the present invention to provide a radiative cooling device including a radiative cooling layer having an uneven pattern and a method of manufacturing the radiative cooling device. According to the present invention, due to increase in the surface area of the radiative cooling layer due to the presence of the uneven pattern, the mid-infrared emissivity of the radiative cooling device may be increased, thereby improving cooling efficiency.

It is another object of the present invention to provide a radiative cooling device including a radiative cooling layer formed using an oxide, a nitride, or a polymer capable of emitting mid-infrared light and a method of manufacturing the radiative cooling device. Due to the radiative cooling layer, the mid-infrared emissivity of the radiative cooling device may be increased, and the cooling efficiency thereof may be improved.

It is still another object of the present invention to provide a radiative cooling device including a radiative cooling layer formed using fine particles made of an oxide or a nitride, a polymer, or a mixture of the fine particles and the polymer and a method of manufacturing the radiative cooling device. Due to the radiative cooling layer, mid-infrared emissivity may be increased, thereby improving the cooling efficiency of the radiative cooling device.

It is still another object of the present invention to provide a radiative cooling device including a radiative cooling layer formed of materials having a high refractive index and a low refractive index with respect to visible light, and a method of manufacturing the radiative cooling device. Due to the radiative cooling layer, visible light reflectance may be maximized, thereby improving the cooling efficiency of the radiative cooling device.

It is still another object of the present invention to provide a white radiative cooling device including a white radiative cooling layer containing fine particles made of a metal oxide, or a polymer that reflects and scatters visible light. Due to the white radiative cooling layer, the white radiative cooling device may appear white.

It is still another object of the present invention to provide a white radiative cooling device capable of reflecting all incident sunlight. Due to these features, the cooling performance of the white radiative cooling device may be improved.

It is still another object of the present invention to provide a white radiative cooling device including a white radiative cooling layer including a polymer matrix and fine particles including a polymer. Due to the white radiative cooling layer, mass production may be easy, manufacturing cost may be reduced, and various physical properties may be adjusted.

It is still another object of the present invention to provide a white radiative cooling device including a reflection enhancement layer on the lower surface of a white radiative cooling layer. Due to the reflection enhancement layer, visible light reflectance may be increased, thereby improving the cooling performance of the white radiative cooling device.

It is yet another object of the present invention to provide a white radiative cooling device including a white radiative cooling layer including fluorescent particles. Due to the white radiative cooling layer, the white radiative cooling device may exhibit a variety of colors in addition to white.

Technical Solution

In accordance with one aspect of the present invention, provided is a radiative cooling device including a reflective layer formed on a substrate and responsible for reflecting sunlight having wavelengths corresponding to ultraviolet, visible, and near-infrared regions; and a radiative cooling layer formed on the reflective layer and responsible for absorbing sunlight having a wavelength corresponding to a mid-infrared region and emitting the sunlight as heat, wherein the radiative cooling layer includes a first radiation layer including an uneven pattern; and a second radiation layer formed on the first radiation layer and having a refractive index different from that of the first radiation layer.

According to the radiative cooling device according to an embodiment of the present invention, in the radiative cooling layer, the first radiation layer and the second radiation layer may be repeatedly formed.

According to the radiative cooling device according to an embodiment of the present invention, the reflective layer may include at least one of silver (Ag), aluminum (Al), and platinum (Pt).

According to the radiative cooling device according to an embodiment of the present invention, each of the first radiation layer and the second radiation layer may include at least one of fine particles made of an oxide or a nitride and a polymer.

According to the radiative cooling device according to an embodiment of the present invention, the fine particles may have a diameter of 10 nm to 20 μm.

According to the radiative cooling device according to an embodiment of the present invention, the fine particles may include at least one of silica ($SiO_2$), zirconium oxide ($ZrO_2$), alumina ($Al_2O_3$), titanium dioxide ($TiO_2$), and silicon nitride ($Si_3N_4$).

According to the radiative cooling device according to an embodiment of the present invention, the polymer may be polydimethylsiloxane (PDMS) or dipentaerythritol penta/hexa acrylate (DPHA).

According to the radiative cooling device according to an embodiment of the present invention, each of the first radiation layer and the second radiation layer may have a thickness of 10 nm to 2,000 nm.

According to the radiative cooling device according to an embodiment of the present invention, the radiative cooling layer may include a mid-infrared light absorption layer formed on the reflective layer and responsible for absorbing sunlight having a wavelength corresponding to a mid-infrared region and emitting the sunlight as heat; and a coating layer formed on the mid-infrared light absorption layer and including a first coating layer and a second coating layer having different refractive indexes with respect to sunlight having a wavelength corresponding to a visible region. In this case, the first coating layer may have a greater refractive index than the second coating layer with respect to sunlight having a wavelength corresponding to a visible region.

According to the radiative cooling device according to an embodiment of the present invention, the coating layer may reflect sunlight having a wavelength corresponding to a visible region.

According to the radiative cooling device according to an embodiment of the present invention, in the coating layer, the first coating layer and the second coating layer may be repeatedly formed.

According to the radiative cooling device according to an embodiment of the present invention, a difference in refractive index between the first coating layer and the second coating layer may be 0.7 to 2.

According to the radiative cooling device according to an embodiment of the present invention, the first coating layer may include at least one of ZnS, Si, and Ge, and the second coating layer may include $CaF_2$.

In accordance with another aspect of the present invention, provided is a method of manufacturing a radiative cooling device, the method including a step of forming a reflective layer for reflecting sunlight having wavelengths corresponding to ultraviolet, visible, and near-infrared regions on a substrate; and a step of forming, on the reflective layer, a radiative cooling layer for absorbing sunlight having a wavelength corresponding to a mid-infrared region and emitting the sunlight as heat, wherein the step of forming the radiative cooling layer includes a step of forming, on the reflective layer, a first radiation layer including an uneven pattern; and a step of forming, on the first radiation layer, a second radiation layer having a refractive index different from that of the first radiation layer.

According to the method of manufacturing a radiative cooling device according to an embodiment of the present invention, the radiative cooling layer may be formed on the reflective layer, and the first radiation layer and the second radiation layer may be repeatedly formed in the radiative cooling layer.

According to the method of manufacturing a radiative cooling device according to an embodiment of the present invention, the first radiation layer may be formed to have an uneven pattern using a stamp after the reflective layer is coated with at least one of fine particles made of an oxide or a nitride and a polymer.

According to the method of manufacturing a radiative cooling device according to an embodiment of the present invention, the second radiation layer may be formed by spin-coating at least one of fine particles made of an oxide or a nitride and a polymer on the substrate.

According to the method of manufacturing a radiative cooling device according to an embodiment of the present invention, the spin coating may be performed for 30 to 40 seconds.

According to the method of manufacturing a radiative cooling device according to an embodiment of the present invention, the step of forming the radiative cooling layer may include a step of forming, on the reflective layer, a mid-infrared light absorption layer for absorbing sunlight having a wavelength corresponding to a mid-infrared region and emitting the sunlight as heat; and a step of forming, on the mid-infrared light absorption layer, a coating layer for reflecting sunlight having a wavelength corresponding to a visible region. In the step of forming the coating layer, a first coating layer and a second coating layer having different refractive indexes with respect to sunlight having a wavelength corresponding to a visible region may be formed on the mid-infrared light absorption layer. In this case, the first coating layer may have a greater refractive index than the second coating layer with respect to sunlight having a wavelength corresponding to a visible region.

According to the method of manufacturing a radiative cooling device according to an embodiment of the present invention, in the coating layer, the first coating layer and the second coating layer may be repeatedly formed.

In accordance with still another aspect of the present invention, provided is a white radiative cooling device including a substrate; and a white radiative cooling layer formed on the substrate, wherein, in the white radiative cooling layer, fine particles including a metal oxide or a polymer that reflects and scatters sunlight having a wavelength corresponding to a visible region are embedded in a polymer matrix that absorbs sunlight having a wavelength corresponding to a mid-infrared region and emits the sunlight as heat, wherein the white radiative cooling layer absorbs sunlight having a wavelength corresponding to a mid-infrared region and emits the sunlight as heat while reflecting and scattering sunlight having a wavelength corresponding to a visible region.

According to the white radiative cooling device according to an embodiment of the present invention, the white radiative cooling device may become white due to reflection and scattering of sunlight having a wavelength corresponding to a visible region by the metal oxide-containing fine particles included in the white radiative cooling layer.

According to the white radiative cooling device according to an embodiment of the present invention, the polymer matrix and the fine particles including the polymer may have different refractive indexes, and the white radiative cooling device may become white due to reflection and scattering of sunlight having a wavelength corresponding to a visible region by the polymer-containing fine particles included in the white radiative cooling layer.

According to the white radiative cooling device according to an embodiment of the present invention, the polymer matrix may include at least one of polydimethylsiloxane (PDMS), polymethyl methacrylate (PMMA), dipentaerythritol penta/hexa acrylate (DPHA), polyvinylidene fluoride (PVDF), and polyurethane acrylate (PUA).

According to the white radiative cooling device according to an embodiment of the present invention, the metal oxide may include at least one of titanium dioxide (TiO$_2$), zirconium oxide (ZrO$_2$), alumina (Al$_2$O$_3$), and zinc oxide (ZnO).

According to the white radiative cooling device according to an embodiment of the present invention, the polymer may include at least one of polyvinylidene fluoride (PVDF) and polyurethane acrylate (PUA).

According to the white radiative cooling device according to an embodiment of the present invention, the white radiative cooling device may further include, on a lower surface of the white radiative cooling layer, a reflection enhancement layer for additionally reflecting sunlight having a wavelength corresponding to a visible region.

According to the white radiative cooling device according to an embodiment of the present invention, the reflection enhancement layer may include at least one of silver (Ag), aluminum (Al), and platinum (Pt).

According to the white radiative cooling device according to an embodiment of the present invention, in the white radiative cooling device, the reflection enhancement layer and the white radiative cooling layer may be repeatedly formed.

In accordance with yet another aspect of the present invention, provided is a white radiative cooling device including a substrate; and a white radiative cooling layer formed on the substrate, wherein, in white radiative cooling layer, metal oxide particles for reflecting and scattering sunlight having a wavelength corresponding to a visible region and fluorescent particles for emitting fluorescence are embedded in a polymer matrix for absorbing sunlight having a wavelength corresponding to a mid-infrared region and emitting the sunlight as heat, wherein the white radiative cooling layer absorbs sunlight having a wavelength corresponding to a mid-infrared region and emits the sunlight as heat while reflecting and scattering sunlight having a wavelength corresponding to a visible region.

Advantageous Effects

According to an embodiment of the present invention, since a radiative cooling layer includes an uneven pattern, the surface area thereof is increased. Accordingly, the mid-infrared emissivity of a radiative cooling device can be increased, thereby improving the cooling efficiency thereof.

According to an embodiment of the present invention, by forming a radiative cooling layer using an oxide, a nitride, or a polymer capable of emitting mid-infrared light, mid-infrared emissivity can be increased, thereby improving the cooling efficiency of a radiative cooling device.

According to an embodiment of the present invention, by forming a radiative cooling layer using fine particles made of an oxide or a nitride, a polymer, or a mixture of the fine particles and the polymer, mid-infrared emissivity can be increased, thereby improving the cooling efficiency of a radiative cooling device.

According to an embodiment of the present invention, by forming a radiative cooling layer using materials having a high refractive index and a low refractive index with respect to visible light, visible light reflectance can be maximized, thereby improving the cooling efficiency of a radiative cooling device.

According to an embodiment of the present invention, by forming a white radiative cooling layer including fine particles made of a metal oxide, or a polymer that reflects and scatters visible light, a radiative cooling device can appear white.

According to an embodiment of the present invention, by reflecting all incident sunlight, cooling performance can be improved.

According to an embodiment of the present invention, by forming a white radiative cooling layer including a polymer matrix and fine particles including a polymer, mass production can be easy, manufacturing cost can be reduced, and various physical properties can be adjusted.

According to an embodiment of the present invention, by including a reflection enhancement layer on the lower surface of a white radiative cooling layer, visible light reflectance can be increased, thereby improving cooling performance.

According to an embodiment of the present invention, by forming a white radiative cooling layer including fluorescent particles, a white radiative cooling device can exhibit a variety of colors in addition to white.

BEST MODE

Figure 1A:
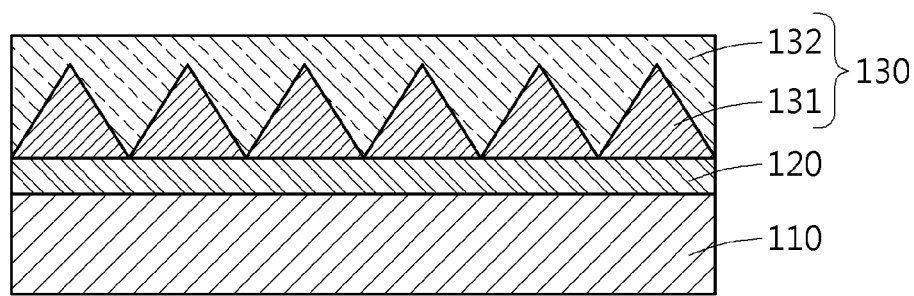
FIGS. 1A and 1B each show a cross-sectional view of a radiative cooling device according to an embodiment of the present invention.

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the disclosure and the appended claims, the singular form "a" or "an" is intended to include the plural forms as well, unless context clearly indicates otherwise.

Although terms used in the specification are selected from terms generally used in related technical fields, other terms may be used according to technical development and/or due to change, practices, priorities of technicians, etc. Therefore, it should not be understood that terms used below limit the technical spirit of the present invention, and it should be understood that the terms are exemplified to describe embodiments of the present invention.

Also, some of the terms used herein may be arbitrarily chosen by the present applicant. In this case, these terms are defined in detail below. Accordingly, the specific terms used herein should be understood based on the unique meanings thereof and the whole context of the present invention.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

In addition, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

A radiative cooling device according to an embodiment of the present invention absorbs mid-infrared light and emits the absorbed mid-infrared light as heat, and is formed on the surface of an object so that the temperature of the object located under the radiative cooling device according to an embodiment of the present invention is lower than external temperature.

For example, the radiative cooling device according to an embodiment of the present invention may be formed on the surface of an automobile to make the temperature of the frame of the automobile lower than external temperature, or to make the temperature inside of the automobile lower than external temperature.

In this case, the object is an object equipped with the radiative cooling device, and may be an automobile, a building such as an apartment, a shopping mall, or an office building, or a pipe for heat exchange provided in an air/water cooling chiller.

Any objects on which the radiative cooling device according to an embodiment of the present invention is mountable may be used as the object of the present invention, without being limited thereto.

In this case, external temperature means atmospheric temperature (ambient temperature), and may be the external temperature of the radiative cooling device according to an embodiment of the present invention.

Figure 1B:
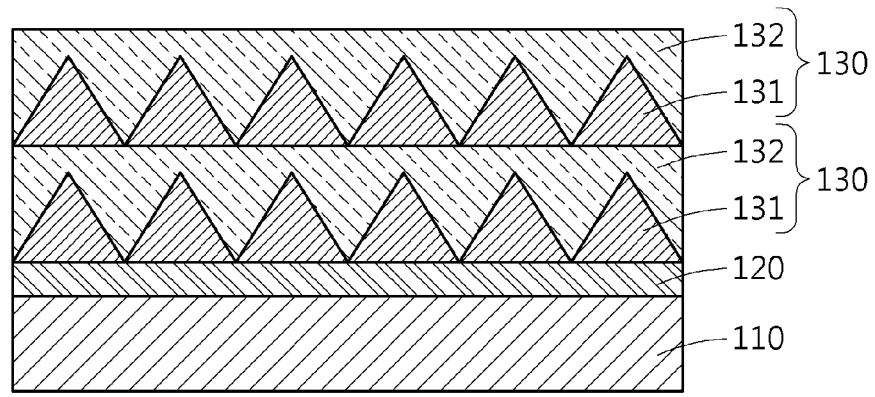

FIGS. 1A and 1B each show a cross-sectional view of a radiative cooling device according to an embodiment of the present invention.

Referring to FIG. 1A, a radiative cooling device 100 according to an embodiment of the present invention includes a reflective layer 120 formed on a substrate 110 and responsible for reflecting sunlight having wavelengths corresponding to ultraviolet, visible, and near-infrared regions and a radiative cooling layer 130 formed on the reflective layer 120 and responsible for absorbing sunlight having a wavelength corresponding to a mid-infrared region and emitting the sunlight as heat.

In general, since the sun has a surface temperature of about 6,000° C., sunlight has various wavelengths corresponding to ultraviolet, visible, and near-infrared regions.

The reflective layer 120 reflects ultraviolet light, visible light, and near-infrared light of sunlight to prevent the temperature of the radiative cooling device 100 according to an embodiment of the present invention from being increased by sunlight.

That is, the reflective layer 120 may reflect sunlight to minimize sunlight absorbed by the radiative cooling device 100 according to an embodiment of the present invention and maximize reflection of sunlight.

The reflective layer 120 may be formed of a material capable of effectively reflecting sunlight, and in particular, is preferably formed of a material having a reflectance of 90% or more with respect to visible light.

For example, the reflective layer 120 may be formed of at least one metal material of silver (Ag), aluminum (Al), and platinum (Pt), without being limited thereto.

According to an embodiment, the reflective layer 120 may be formed of a commercially available solar reflective film such as a Solar mirror film manufactured by 3M.

According to an embodiment, the reflective layer 120 may be formed of a multilayer thin film formed of a polymer or an inorganic material.

The multilayer thin film may have a form in which materials having different refractive indexes are repeatedly laminated.

According to an embodiment, the substrate 110 may be formed of any one of a flexible polymer film, glass, quartz, silicon wafer, and metal, without being limited thereto.

For example, the substrate 110 may be formed of any one of polyester-based resins such as polyethylene naphthalate (PEN), acetate-based resins, polyethersulfone-based resins, polycarbonate-based resins, polyamide-based resins, polyimide-based resins, polyolefin-based resins, (meth)acrylic resins, polyvinyl chloride-based resins, polyvinylidene chloride-based resins, polystyrene-based resins, polyvinyl alcohol-based resins, polyarylate-based resins, and polyphenylene sulfide-based resins.

The radiative cooling layer 130 may be formed on the reflective layer 120 to absorb mid-infrared light and emit the mid-infrared light as heat, so that the temperature of an object provided with the radiative cooling device 100 according to an embodiment of the present invention is decreased.

In general, since objects on the earth have a surface temperature of several tens of degrees C., these objects emit mid-infrared light with a wavelength of 8 μm to 13 μm.

Such mid-infrared radiation may lower the temperature of an object, and the radiative cooling device 100 according to an embodiment of the present invention includes the radiative cooling layer 130 formed of a material capable of effectively emitting mid-infrared light of the atmospheric window corresponding to a wavelength range of 8 μm to 13 μm, so that the temperature of the object is kept lower than external temperature.

The radiative cooling layer 130 according to an embodiment of the present invention may be formed of a material capable of effectively emitting mid-infrared light and may be formed in a single layer.

According to an embodiment, the radiative cooling layer 130 is formed by laminating two thin films formed of two different materials capable of effectively emitting mid-infrared light, and may include a first radiation layer 131 and a second radiation layer 132.

Specifically, the first radiation layer 131 may be formed as a thin film on the reflective layer 120. According to an embodiment, the first radiation layer 131 may include an uneven pattern and may be formed on the reflective layer 120.

When the first radiation layer 131 includes an uneven pattern, the surface area of the first radiation layer 131 may be increased, thereby increasing mid-infrared emissivity.

The uneven pattern may be an uneven pattern including a plurality of cylindrical shapes, prismatic shapes, or line shapes, without being limited thereto.

The second radiation layer 132 may be formed as a thin film on the first radiation layer 131.

According to an embodiment, the second radiation layer 132 may be formed as a thin film on the first radiation layer 131 including an uneven pattern.

The second radiation layer 132 may be formed of a material having a refractive index different from that of the first radiation layer 131 with respect to sunlight having a wavelength corresponding to a mid-infrared region.

That is, since materials forming the first radiation layer 131 and the second radiation layer 132 have different refractive indexes, high mid-infrared emissivity may be achieved by the phonon-polariton resonance effect.

According to an embodiment, with respect to sunlight having a wavelength corresponding to a mid-infrared region, a difference in refractive index between the first radiation layer 131 and the second radiation layer 132 may be 0.7 to 2.

The first radiation layer 131 and the second radiation layer 132 according to an embodiment of the present invention may include at least one of an oxide, a nitride, or a polymer.

In this case, the materials forming the first radiation layer 131 and the second radiation layer 132 may be different.

The oxide may include silica ($SiO_2$), zirconium oxide ($ZrO_2$), alumina ($Al_2O_3$), and titanium dioxide ($TiO_2$), without being limited thereto.

The nitride may be silicon nitride ($Si_3N_4$), without being limited thereto.

According to an embodiment, the polymer may be an acrylic polymer such as polydimethylsiloxane (PDMS) or dipentaerythritol penta/hexa acrylate (DPHA), without being limited thereto.

The acrylic polymer has C—O stretching vibration, and thus has high emissivity in a wavelength corresponding to a mid-infrared region.

In particular, DPHA has high emissivity in a wavelength corresponding to a mid-infrared region due to C—O stretching vibration and C=C bending vibration.

For example, the first radiation layer 131 may be a layer formed by depositing silica, which is an oxide, and the second radiation layer 132 may be a layer formed by depositing alumina, without being limited thereto.

Alternatively, the first radiation layer 131 may be a layer formed by performing spin coating using PDMS, and the second radiation layer 132 may be a layer formed by depositing silicon nitride, without being limited thereto.

The first radiation layer 131 and the second radiation layer 132 according to an embodiment of the present invention may include at least one of fine particles and a polymer.

According to an embodiment, the first radiation layer 131 or the second radiation layer 132 may be formed of a mixture of the fine particles and the polymer.

As the content of the fine particles in the mixture increases, emissivity of mid-infrared light may be increased.

Based on a total weight of the mixture, 1% by weight to 20% by weight of the fine particles may be mixed with the polymer.

When the content of the fine particles exceeds 20% by weight, mid-infrared emissivity no longer increases.

The fine particles may be formed of an oxide or a nitride, and may include, for example, at least one of silica ($SiO_2$), zirconium oxide ($ZrO_2$), alumina ($Al_2O_3$), titanium dioxide ($TiO_2$), and silicon nitride ($Si_3N_4$).

As the size of the fine particles included in the radiative cooling layer 130 decreases, the mid-infrared emissivity of the radiative cooling device 100 according to an embodiment of the present invention may be increased.

According to an embodiment, the fine particles may have a diameter of 10 nm to 20 μm.

Preferably, the fine particles having a nanometer-scale diameter may have higher mid-infrared emissivity than the fine particles having a micrometer-scale diameter.

For example, the first radiation layer 131 may be formed of a mixture of the fine particles and the polymer, and the second radiation layer 132 may be formed of the polymer.

For example, the first radiation layer 131 may be formed of fine particles made of alumina and PDMS as a polymer and the second radiation layer 132 may be formed of silicon nitride ($Si_3N_4$) as a polymer without being limited thereto.

As another example, the first radiation layer 131 and the second radiation layer 132 may be formed of a mixture of the fine particles and the polymer. In this case, the types of the fine particles and the polymer forming the first radiation layer 131 and the second radiation layer 132 may be different.

For example, the first radiation layer 131 may be formed of a mixture of fine particles made of silica and PDMS as a polymer, and the second radiation layer 132 may be formed of fine particles made of alumina and DPHA as a polymer, without being limited thereto.

The first radiation layer 131 and the second radiation layer 132 may have the same thickness or may have different thicknesses.

According to an embodiment, each of the first radiation layer 131 and the second radiation layer 132 may be formed to have a thickness of 10 nm to 2,000 nm.

In this case, when the first radiation layer 131 includes an uneven pattern, the height from the surface of the reflective layer 120 to the uppermost end of the convex portion (凸) of the uneven pattern may be set as the thickness of the first radiation layer 131.

According to an embodiment, the radiative cooling layer 130 may include the first radiation layer 131, the second radiation layer 132, and a third radiation layer (not shown).

According to an embodiment, the first radiation layer 131, the second radiation layer 132 and the third radiation layer may emit mid-infrared light, and may be formed of materials having different refractive indexes.

Referring to FIG. 1B, the radiative cooling device 100 according to an embodiment of the present invention may include the radiative cooling layer 130 in which the first radiation layer 131 and the second radiation layer 132 are repeatedly formed.

For example, the radiative cooling layer 130 may be formed by repeatedly laminating the first radiation layer 131 and the second radiation layer 132 on the reflective layer 120 in the order of the first radiation layer 131-the second radiation layer 132-the first radiation layer 131-the second radiation layer 132.

According to an embodiment, although not shown in the drawings, the radiative cooling layer 130 may be formed by repeatedly laminating the first radiation layer 131 and the second radiation layer 132 on the reflective layer 120 in the order of the first radiation layer 131-the second radiation layer 132-the first radiation layer 131-the second radiation layer 132-the first radiation layer 131-the second radiation layer 132-the first radiation layer 131-the second radiation layer 132 - . . . .

For example, the radiative cooling layer 130 may be formed by repeatedly laminating, on the reflective layer 120, a unit layer consisting of alumina, silicon nitride, and silica in the order of alumina-silicon nitride-silica.

As another example, the radiative cooling layer 130 may be formed by repeatedly laminating a unit layer consisting of PDMS, silicon nitride, and silica in the order of PDMS-silicon nitride-silica.

The first radiation layer 131 and the second radiation layer 132 have been described with reference to FIG. 1A, and thus repeated description thereof will be omitted.

Since the radiative cooling device 100 according to an embodiment of the present invention includes the reflective layer 120 for reflecting ultraviolet light, visible light, and near-infrared light of sunlight and the radiative cooling layer 130 formed of a material that emits mid-infrared light, the radiative cooling device 100 may efficiently emit mid-infrared light, and thus may efficiently cool an object without energy consumption.

Hereinafter, the structure and properties of the radiative cooling device according to another embodiment of the present invention will be described.

Figure 2A:
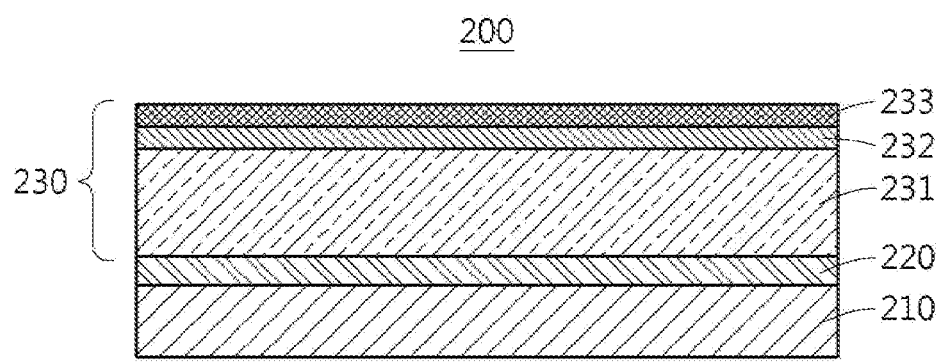
FIGS. 2A and 2B each show a cross-sectional view of a radiative cooling device according to another embodiment of the present invention.
Figure 2B:
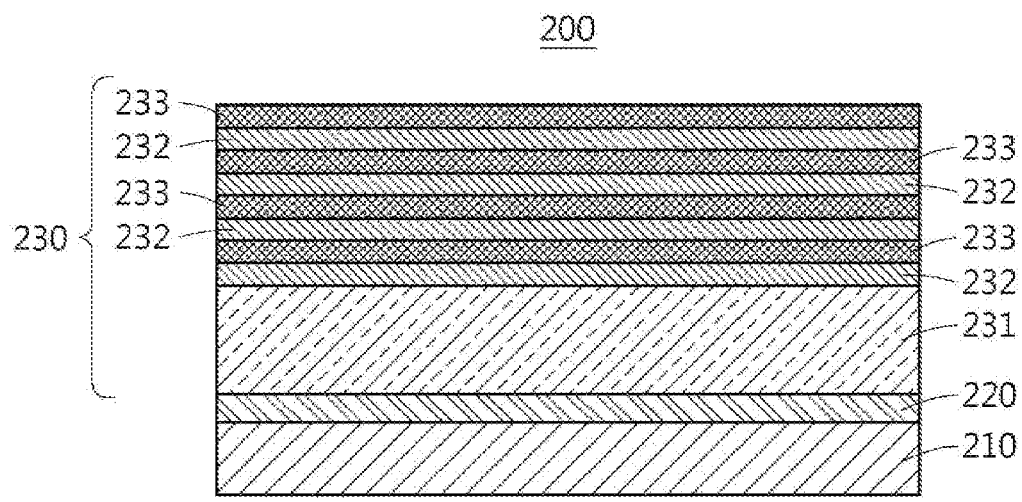

FIGS. 2A and 2B each show a cross-sectional view of a radiative cooling device according to another embodiment of the present invention.

Referring to FIG. 2A, in a radiative cooling device 200 according to another embodiment of the present invention, a radiative cooling layer 230 may include a mid-infrared light absorption layer 231 formed on a reflective layer 220 and responsible for absorbing sunlight having a wavelength corresponding to a mid-infrared region and emitting the sunlight as heat and a coating layer formed on the mid-infrared light absorption layer 231 and responsible for reflecting visible light.

The mid-infrared light absorption layer 231 may be formed on the reflective layer 220 to absorb mid-infrared light and emit the mid-infrared light as heat, so that the temperature of the radiative cooling device 200 according to another embodiment of the present invention may be decreased.

The mid-infrared light absorption layer 231 may be formed of a material capable of effectively emitting mid-infrared light and may be formed in a single layer.

The material forming the mid-infrared light absorption layer 231 may have high emissivity with respect to mid-infrared light, and may be transparent with respect to sunlight having wavelengths corresponding to ultraviolet, visible, and near-infrared regions.

According to an embodiment, the mid-infrared light absorption layer 231 may be formed of a polymer.

For example, the polymer may be polydimethylsiloxane (PDMS) or dipentaerythritol penta/hexa acrylate (DPHA).

According to an embodiment, the mid-infrared light absorption layer 231 may be formed of at least one of an oxide, a nitride, and a polymer.

The oxide may include silica ($SiO_2$), zirconium oxide ($ZrO_2$), alumina ($Al_2O_3$), and titanium dioxide ($TiO_2$), without being limited thereto.

The nitride may be silicon nitride ($Si_3N_4$), without being limited thereto.

According to an embodiment, the polymer may be polydimethylsiloxane (PDMS) or dipentaerythritol penta/hexa acrylate (DPHA).

For example, the mid-infrared light absorption layer 231 may be a layer formed by depositing silica, which is an oxide, without being limited thereto.

As another example, the mid-infrared light absorption layer 231 may be formed by performing spin coating using PDMS as a polymer, without being limited thereto.

According to an embodiment, the mid-infrared light absorption layer 231 may be formed of a mixture of fine particles and a polymer.

The fine particles may be made of an oxide or a nitride. For example, the fine particles may include at least one of silica ($SiO_2$), zirconium oxide ($ZrO_2$), alumina ($Al_2O_3$), titanium dioxide ($TiO_2$), and silicon nitride ($Si_3N_4$).

As the size of the fine particles included in the radiative cooling layer 230 decreases, the mid-infrared emissivity of the radiative cooling device 200 according to an embodiment of the present invention may be increased.

According to an embodiment, the fine particles may have a diameter of 10 nm to 20 μm.

For example, the mid-infrared light absorption layer 231 may be formed of PDMS or DPHA, and may be a single layer formed by performing spin coating using a mixture of PDMS and DPHA.

Alternatively, the mid-infrared light absorption layer 231 may be a single layer formed by performing spin coating using a mixture of fine particles made of silica and PDMS as a polymer.

The coating layer serves to reflect visible light. For effective reflection of visible light, the coating layer may be formed of a material having a high refractive index with respect to visible light.

In this case, the high refractive index may be a refractive index of 1.5 or more with respect to visible light.

Accordingly, the coating layer may be a layer formed of a material having a refractive index of 1.5 or more with respect to visible light.

Specifically, the coating layer may be a layer formed of a material having a refractive index of 1.6 to 6 with respect to visible light.

The coating layer may be formed of a defect-free single crystal ceramic material, and may be formed of a material that is transparent to visible light and mid-infrared light.

For example, the coating layer may be formed of at least one of yttria ($Y_2O_3$), ALON, spinel-structured Mg, Si, Ge, ZnS, ZnSe, NaCl, $CaF_2$, KBr, PE, and PS, without being limited thereto.

The coating layer may be formed of a material having a high refractive index with respect to visible light, and is preferably formed of at least one of ZnS, Si, and Ge.

The coating layer according to an embodiment of the present invention is formed of a material having a higher refractive index than that of the mid-infrared light absorption layer 231 to efficiently reflect visible light. Accordingly, the heat absorptivity of the radiative cooling device 200 according to another embodiment of the present invention may be reduced, thereby improving cooling efficiency.

According to an embodiment, the coating layer may be formed of multiple layers formed of materials having different refractive indexes with respect to visible light.

Specifically, the coating layer may be formed on the mid-infrared light absorption layer 231, and may include a first coating layer 232 and a second coating layer 233 having different refractive indexes with respect to visible light.

The first coating layer 232 may be formed on the mid-infrared light absorption layer 231, and may be formed of a material having a higher refractive index than that of the second coating layer 233 with respect to visible light.

The second coating layer 233 may be formed on the first coating layer 232, and may be formed of a material having a lower refractive index than that of the first coating layer 232 with respect to visible light.

Specifically, a difference in refractive index between the first coating layer 232 and the second coating layer 233 may be 0.7 to 2.

In the radiative cooling device 200 according to another embodiment of the present invention, the second coating layer 233 may be formed on the mid-infrared light absorption layer 231, and the first coating layer 232 may be formed on the second coating layer 233.

According to an embodiment, the first coating layer 232 may be formed of at least one ZnS, Si, Ge, and $ZrO_2$ that have a higher refractive index than that of the second coating layer 233 with respect to visible light, without being limited thereto.

According to an embodiment, the second coating layer 233 may be formed of at least one of $CaF_2$ and $SiO_2$ that have a lower refractive index than that of the first coating layer 232 with respect to visible light, without being limited thereto.

The first coating layer 232 and the second coating layer 233 included in the coating layer have different refractive indexes with respect to visible light. Accordingly, the coating layer may have high reflectance with respect to visible light.

The first coating layer 232 and the second coating layer 233 are formed of materials having high or low refractive indexes with respect to visible light to maximize reflection of visible light and minimize visible light reaching the reflective layer 220. Accordingly, the cooling efficiency of the radiative cooling device 200 according to another embodiment of the present invention may be improved.

Referring to FIG. 2B, a radiative cooling device according to another embodiment of the present invention may include a coating layer in which a first coating layer and a second coating layer are repeatedly formed.

Specifically, the coating layer may be formed by repeatedly laminating the first coating layer and the second coating layer on a mid-infrared light absorption layer in the order of the first coating layer—the second coating layer—the first coating layer—the second coating layer—the first coating layer—the second coating layer - . . . .

According to an embodiment, the repeatedly laminated first and second coating layers may be formed of different materials.

The first coating layer and the second coating layer have been described with reference to FIG. 2A, and thus repeated description thereof will be omitted.

Since the coating layer includes the repeated formed first and second coating layers having a high or low refractive index with respect to visible light, reflection of visible light may be maximized, and thus the cooling efficiency of the radiative cooling device according to another embodiment of the present invention may be improved.

The radiative cooling device according to an embodiment of the present invention may reflect 95% or more of sunlight and emit 90% or more of mid-infrared light, and thus may cool an object without energy consumption.

Hereinafter, a method of manufacturing the radiative cooling device according to an embodiment of the present invention will be described.

Since the method of manufacturing the radiative cooling device according to an embodiment of the present invention includes all components of the above-described radiative cooling device, repeated description thereof will be omitted.

Figure 3:
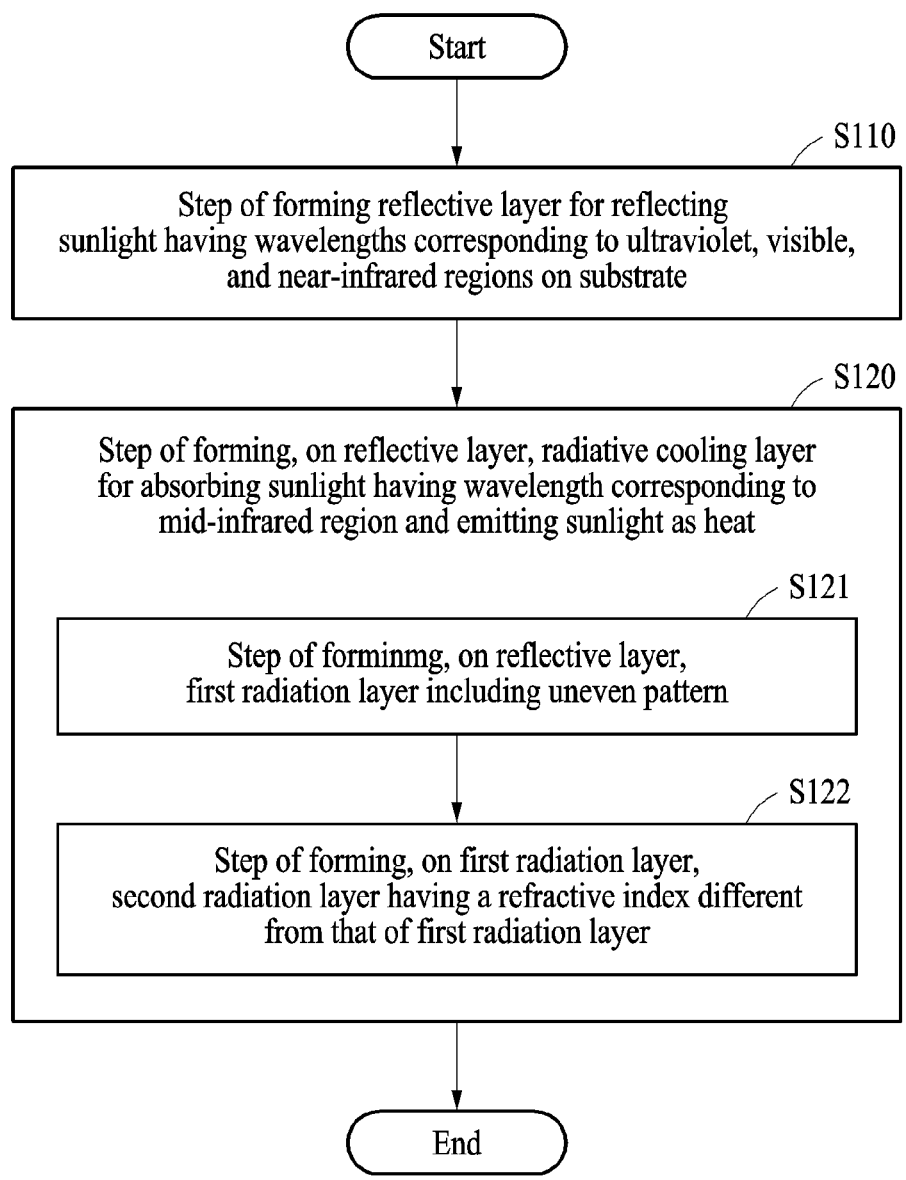
FIG. 3 is a flowchart for explaining a method of manufacturing a radiative cooling device according to an embodiment of the present invention.

FIG. 3 is a flowchart for explaining a method of manufacturing a radiative cooling device according to an embodiment of the present invention.

Referring to FIG. 3, the method of manufacturing the radiative cooling device according to an embodiment of the present invention includes step S110 of forming a reflective layer responsible for reflecting sunlight having wavelengths corresponding to ultraviolet, visible, and near-infrared regions on a substrate and step S120 of forming, on the reflective layer, a radiative cooling layer for absorbing sunlight having a wavelength corresponding to a mid-infrared region and emitting the sunlight as heat.

The substrate may be formed of any one of a flexible polymer film, glass, quartz, silicon wafer, and metal, without being limited thereto.

The substrate has been described with reference to FIG. 1A, and thus repeated description thereof will be omitted.

In step S110, the reflective layer may be formed by depositing a metal material such as silver (Ag), aluminum (Al), and platinum (Pt) on the substrate.

A method of depositing the reflective layer under a reduced pressure, atmospheric pressure, or increased pressure may include sputtering, atomic layer deposition (ALD), chemical vapor deposition (CVD), thermal evaporation, co-evaporation, plasma enhanced chemical vapor deposition (PECVD), e-beam evaporation, radio frequency (RF) sputtering, magnetron sputtering, vacuum deposition, or chemical vapor deposition, without being limited thereto.

In step S120, the reflective layer may be coated with a material that emits mid-infrared light to form the radiative cooling layer.

According to an embodiment, in step S120, the radiative cooling layer having a multilayer form including the first radiation layer and the second radiation layer may be formed on the reflective layer using different materials that emit mid-infrared light.

That is, in step S120, the first radiation layer and the second radiation layer may be formed on the reflective layer using at least one of an oxide, a nitride, and a polymer.

When the first radiation layer and the second radiation layer include an oxide or a nitride, the first radiation layer and the second radiation layer may be formed using a deposition method.

For example, the first radiation layer may be a layer formed by depositing silica, which is an oxide, and the second radiation layer may be a layer formed by depositing alumina.

The deposition method may include, under a reduced pressure, atmospheric pressure, or increased pressure, sputtering, atomic layer deposition (ALD), chemical vapor deposition (CVD), thermal evaporation, co-evaporation, plasma enhanced chemical vapor deposition (PECVD), e-beam evaporation, radio frequency (RF) sputtering, magnetron sputtering, vacuum deposition, or chemical vapor deposition, without being limited thereto.

When the first radiation layer and the second radiation layer include a polymer, the first radiation layer and the second radiation layer may be formed using a coating method.

For example, the first radiation layer may be a layer formed by performing spin coating using PDMS, and the second radiation layer may be a layer formed by depositing silicon nitride, which is a nitride.

The coating method may include any one of spin coating, spray coating, ultra-spray coating, electrospinning coating, slot die coating, gravure coating, bar coating, roll coating, dip coating, shear coating, screen-printing, inkjet printing, and nozzle printing, without being limited thereto.

According to an embodiment, the first radiation layer and the second radiation layer may include at least one of fine particles and a polymer.

For example, the first radiation layer may be formed of a mixture of the fine particles and the polymer, and the second radiation layer may be formed of the polymer.

When the first radiation layer and the second radiation layer include a mixture of the fine particles and the polymer, the first radiation layer and the second radiation layer may be formed using a coating method.

The coating method may be spin coating, or may include any one of spray coating, ultra-spray coating, electrospinning coating, slot die coating, gravure coating, bar coating, roll coating, dip coating, shear coating, screen-printing, inkjet printing, and nozzle printing, without being limited thereto.

According to an embodiment, the first radiation layer may have a large surface area by including an uneven pattern, and thus may improve mid-infrared emissivity.

Specifically, step S120 may include step S121 of forming, on the reflective layer, a first radiation layer including an uneven pattern and step S122 of forming, on the first radiation layer, a second radiation layer having a refractive index different from that of the first radiation layer.

In step S121, using at least one of the fine particles made of an oxide or a nitride and the polymer, the first radiation layer including an uneven pattern may be formed on the reflective layer.

In step S121, using a stamp having a pattern corresponding to the uneven pattern, the first radiation layer including an uneven pattern may be formed on the reflective layer through an optical-based lithography process or a non-optical-based lithography process.

The optical-based lithography process may be any one of photolithography, laser interference lithography, and e-beam lithography, without being limited thereto.

The non-optical-based lithography process may be any one of nanoimprint lithography, nanotransfer printing, and roll imprint lithography, without being limited thereto.

According to an embodiment, in step S121, coating is performed using at least one of the fine particles made of an oxide or a nitride and the polymer, and then an uneven pattern may be formed by performing cutting in a top-down manner.

The uneven pattern may be an uneven pattern including a plurality of cylindrical shapes, prismatic shapes, or line shapes, without being limited thereto.

In step S122, using a material having a refractive index different from that of the first radiation layer, the second radiation layer may be formed on the first radiation layer including an uneven pattern.

Specifically, in step S122, to form the second radiation layer, the first radiation layer may be spin-coated with a material having a refractive index different from that of the first radiation layer.

In step S122, the thickness of the second radiation layer may be determined by adjusting spin coating time.

According to an embodiment, spin coating may be performed for 30 to 40 seconds.

In this case, even when spin coating time exceeds 40 seconds, the thickness of the second radiation layer no longer increases.

According to an embodiment, in the method of manufacturing the radiative cooling device according to an embodiment of the present invention, step S121 and step S122 may be repeatedly performed to form a radiative cooling layer in which the first radiation layer and the second radiation layer are repeatedly formed.

Specifically, the first radiation layer having a layer form or including an uneven pattern may be formed on the reflective layer, the second radiation layer having a layer form may be formed on the first radiation layer, the first radiation layer having a layer form or including an uneven pattern may be formed on the second radiation layer again, and then the second radiation layer may be formed thereon.

According to the method of manufacturing the radiative cooling device according to an embodiment of the present invention, a radiative cooling device having a simple structure including a small number of layers may be manufactured through a simple process.

The radiative cooling device manufactured by the method of manufacturing a radiative cooling device according to an embodiment of the present invention has a large surface area due to an uneven pattern included in the radiative cooling layer. Accordingly, mid-infrared radiation may be increased, and thus cooling efficiency may be improved.

Hereinafter, the method of manufacturing a radiative cooling device according to another embodiment of the present invention will be described.

The method of manufacturing a radiative cooling device according to another embodiment of the present invention includes the components of the radiative cooling device described in FIGS. 2A and 2B, and thus repeated description thereof will be omitted.

Figure 4:
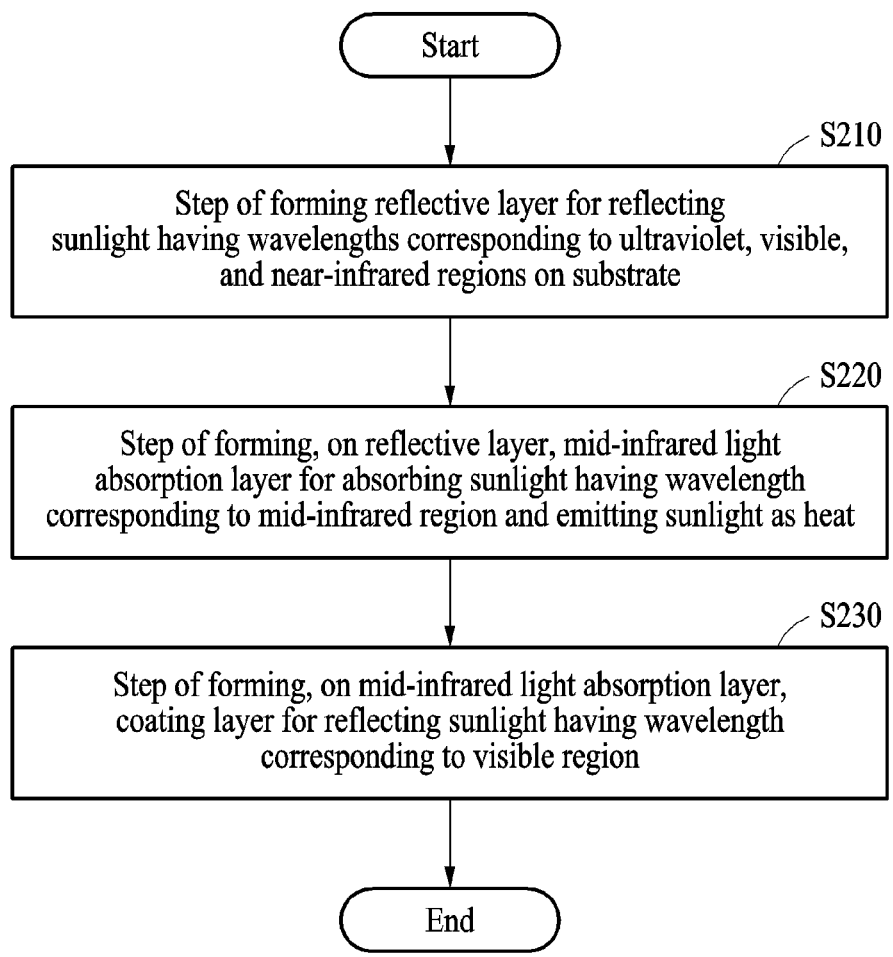
FIG. 4 is a flowchart for explaining a method of manufacturing a radiative cooling device according to another embodiment of the present invention.

FIG. 4 is a flowchart for explaining a method of manufacturing a radiative cooling device according to another embodiment of the present invention.

Referring to FIG. 4, the method of manufacturing a radiative cooling device according to another embodiment of the present invention include step S210 of forming a reflective layer for reflecting sunlight having wavelengths corresponding to ultraviolet, visible, and near-infrared regions on a substrate, step S220 forming, on the reflective layer, a mid-infrared light absorption layer for absorbing sunlight having a wavelength corresponding to a mid-infrared region and emitting the sunlight as heat, and step S230 of forming, on the mid-infrared light absorption layer, a coating layer for reflecting sunlight having a wavelength corresponding to a visible region.

Step S210 includes the components of step S110 described in FIG. 3, and thus repeated description thereof will be omitted.

In steps S220 and S230, by forming the coating layer on the mid-infrared light absorption layer, the radiative cooling layer including the mid-infrared light absorption layer and the coating layer may be formed.

First, in step S220, using a material capable of emitting mid-infrared light, the mid-infrared light absorption layer may be formed on the reflective layer.

The mid-infrared light absorption layer may be a single layer including at least one of an oxide, a nitride, or a polymer.

When the mid-infrared light absorption layer includes an oxide or a nitride, the mid-infrared light absorption layer may be formed using a deposition method.

The deposition method may include, under a reduced pressure, atmospheric pressure, or increased pressure, sputtering, atomic layer deposition (ALD), chemical vapor deposition (CVD), thermal evaporation, co-evaporation, plasma enhanced chemical vapor deposition (PECVD), e-beam evaporation, radio frequency (RF) sputtering, magnetron sputtering, vacuum deposition, or chemical vapor deposition, without being limited thereto.

When the mid-infrared light absorption layer includes a polymer, the mid-infrared light absorption layer may be formed using a coating method.

The coating method may include spin coating, spray coating, ultra-spray coating, electrospinning coating, slot die coating, gravure coating, bar coating, roll coating, dip coating, shear coating, screen-printing, inkjet printing, and nozzle printing.

In step S230, to effectively reflect visible light, the coating layer may be formed of a material having a high refractive index with respect to visible light.

Specifically, in step S230, to effectively reflect visible light, the coating layer may be formed by depositing a material having a high refractive index with respect to visible light on the mid-infrared light absorption layer or by coating the mid-infrared light absorption layer with the material.

The deposition method may include, under a reduced pressure, atmospheric pressure, or increased pressure, sputtering, atomic layer deposition (ALD), chemical vapor deposition (CVD), thermal evaporation, co-evaporation, plasma enhanced chemical vapor deposition (PECVD), e-beam evaporation, radio frequency (RF) sputtering, magnetron sputtering, vacuum deposition, or chemical vapor deposition, without being limited thereto.

The coating method may include spin coating, spray coating, ultra-spray coating, electrospinning coating, slot die coating, gravure coating, bar coating, roll coating, dip coating, shear coating, screen-printing, inkjet printing, and nozzle printing, without being limited thereto.

According to an embodiment, the coating layer may be formed of multiple layers formed of materials having different refractive indexes with respect to visible light.

Specifically, in step S230, the first coating layer and the second coating layer having different refractive indexes with respect to visible light may be formed on the mid-infrared light absorption layer.

Specifically, the first coating layer may be formed on the mid-infrared light absorption layer. In this case, the first coating layer may be formed by applying a material having a higher refractive index than that of the second coating layer with respect to visible light.

The second coating layer may be formed on the first coating layer. In this case, the second coating layer may be formed by applying a material having a lower refractive index than that of the first coating layer with respect to visible light.

In this case, the first coating layer and the second coating layer may be formed using a depositing process or a coating process.

The deposition method and the coating method have been described above, and thus repeated description thereof will be omitted.

According to an embodiment, in the method of manufacturing a radiative cooling device according to another embodiment of the present invention, the first coating layer and the second coating layer may be repeatedly formed.

In the method of manufacturing a radiative cooling device according to another embodiment of the present invention, a radiative cooling device having excellent cooling efficiency may be manufactured through a simple process.

Compared to a conventional radiative cooling device, the radiative cooling device manufactured using the method of manufacturing a radiative cooling device according to another embodiment of the present invention may have a simple structure including a small number of layers and may have excellent cooling efficiency due to high mid-infrared emissivity.

Hereinafter, the radiative cooling devices according to two embodiments of the present invention were manufactured according to examples below, and the properties thereof were evaluated. Based the results, the properties and effects of the radiative cooling device of the present invention were demonstrated.

EXAMPLES AND COMPARATIVE EXAMPLES

Example 1-1

To manufacture a radiative cooling device, a reflective layer made of silver (Ag) was formed on a glass substrate using an e-beam evaporator.

The reflective layer was spin-coated with silica, a first radiation layer having an uneven pattern was formed using a nano-imprinting process, and then the first radiation layer was spin-coated with alumina to form a second radiation layer.

Example 1-2

A radiative cooling device was manufactured in the same manner as in Example 1-1, except that the second radiation layer was spin-coated with silica, a first radiation layer having an uneven pattern was formed using a nano-imprinting process, and then the first radiation layer was spin-coated with alumina to form the second radiation layer once more.

Example 2

To manufacture a radiative cooling device, a reflective layer made of silver (Ag) was formed on a glass substrate using an e-beam evaporator.

Alumina was deposited on the reflective layer to form a first radiation layer, silicon nitride ($Si_3N_4$) was deposited on the first radiation layer to form a second radiation layer, and then silica was deposited on the second radiation layer to form a third radiation layer.

Example 3-1

To manufacture a radiative cooling device, a reflective layer made of silver (Ag) was formed on a glass substrate using an e-beam evaporator.

The reflective layer was spin-coated with PDMS to form a first radiation layer, silica was deposited on the first radiation layer to form a second radiation layer, and then silicon nitride was deposited on the second radiation layer to form a third radiation layer.

Example 3-2

To manufacture a radiative cooling device, a reflective layer made of silver (Ag) was formed on a glass substrate using an e-beam evaporator.

The reflective layer was spin-coated with PDMS to form a first radiation layer, and then silica was deposited on the first radiation layer to form a second radiation layer.

Example 4

To manufacture a radiative cooling device, a reflective layer made of silver (Ag) was formed on a glass substrate using an e-beam evaporator.

10% by weight of silica fine particles having a diameter of 10 μm was added to PDMS to obtain a mixture.

The reflective layer was spin-coated with the mixture to form a single-layer radiative cooling layer.

Example 4-1

To manufacture a radiative cooling device, a reflective layer made of silver (Ag) was formed on a glass substrate using an e-beam evaporator.

The reflective layer was spin-coated with PDMS to form a single-layer radiative cooling layer.

Example 5

To manufacture three types of radiative cooling devices, a reflective layer made of silver (Ag) was formed on a glass substrate using an e-beam evaporator, and the glass substrate on which the reflective layer was formed was prepared in 3 copies.

The three glass substrates were spin-coated with a solution containing 60% by weight of DPHA, a solution containing 80% by weight of DPHA, and a solution containing 90% by weight of DPHA, respectively. Thereby, a single-layer radiative cooling layer was formed on the reflective layer of each glass substrate.

Example 6-1

To manufacture three types of radiative cooling devices, a reflective layer made of silver (Ag) was formed on a glass substrate using an e-beam evaporator, and the glass substrate on which the reflective layer was formed was prepared in 3 copies.

Three types of mixtures were prepared by adding 1.9% by weight of alumina fine particles having a diameter of 20 nm, 3.8% by weight of alumina fine particles having a diameter of 20 nm, and 7.7% by weight of alumina fine particles having a diameter of 20 nm to DPHA, respectively.

The three glass substrates were spin-coated with the three mixtures, respectively. Thereby, a single-layer radiative cooling layer was formed on the reflective layer of each glass substrate.

Example 6-2

To manufacture three types of radiative cooling devices, a reflective layer made of silver (Ag) was formed on a glass substrate using an e-beam evaporator, and the glass substrate on which the reflective layer was formed was prepared in 3 copies.

Three types of mixtures were prepared by adding alumina fine particles having a diameter of 20 nm, alumina fine particles having a diameter of 1 μm, and alumina fine particles having a diameter of 3 μm to DPHA, respectively.

The three glass substrates were spin-coated with the three mixtures, respectively. Thereby, a single-layer radiative cooling layer was formed on the reflective layer of each glass substrate.

Example 7

To manufacture a radiative cooling device, a reflective layer made of silver (Ag) was formed on a glass substrate to have a thickness of 100 nm using an e-beam evaporator.

The reflective layer was spin-coated with silica fine particles to form a second radiation layer having a thickness of 130 nm.

Fine particles made of zirconium oxide were applied to the second radiation layer, and then a first radiation layer including an uneven pattern was formed through a nano-imprinting process.

In this case, the uneven pattern included in the first radiation layer had a width of 24 μm and a height of 10.2 μm.

Example 8

To manufacture a radiative cooling device, a reflective layer made of silver (Ag) was formed on a silicon substrate using an e-beam evaporator.

$ZrO_2$ was deposited on the reflective layer to form a first coating layer, and then $SiO_2$ was deposited on the first coating layer to form a second coating layer.

Comparative Example 1-1

To manufacture a radiative cooling device, a reflective layer made of silver (Ag) was formed on a glass substrate using an e-beam evaporator.

Silica ($SiO_2$) was deposited on the reflective layer to form a first radiation layer of a layer form, and then alumina ($Al_2O_3$) was deposited on the first radiation layer to form a second radiation layer of a layer form.

Comparative Example 1-2

A radiative cooling device was manufactured in the same manner as in Comparative Example 1-1, except that silica was deposited on the second radiation layer to form a first radiation layer of a layer form, and then alumina was deposited to form a second radiation layer of a layer form.

Comparative Example 2

A cooling device was manufactured by forming a reflective layer made of silver (Ag) on a glass substrate using an e-beam evaporator.

Comparative Example 3

A glass substrate.

Comparative Example 4

A radiative cooling device was manufactured in the same manner as in Example 7, except that zirconium oxide was applied to a second radiation layer to form a first radiation layer having a thickness of 7.33 μm.

Comparative Example 5-1

A cooling device was manufactured by forming a reflective layer made of silver (Ag) on a silicon substrate using an e-beam evaporator.

Comparative Example 5-2

A silicon substrate.
Characteristics Evaluation
1. Emissivity of Radiative Cooling Device According to Presence or Absence of Uneven Pattern FIG. 5 is a graph showing absorbance according to whether the first radiation layer and the second radiation layer are repeatedly laminated according to examples and comparative examples of the present invention.

Figure 5:
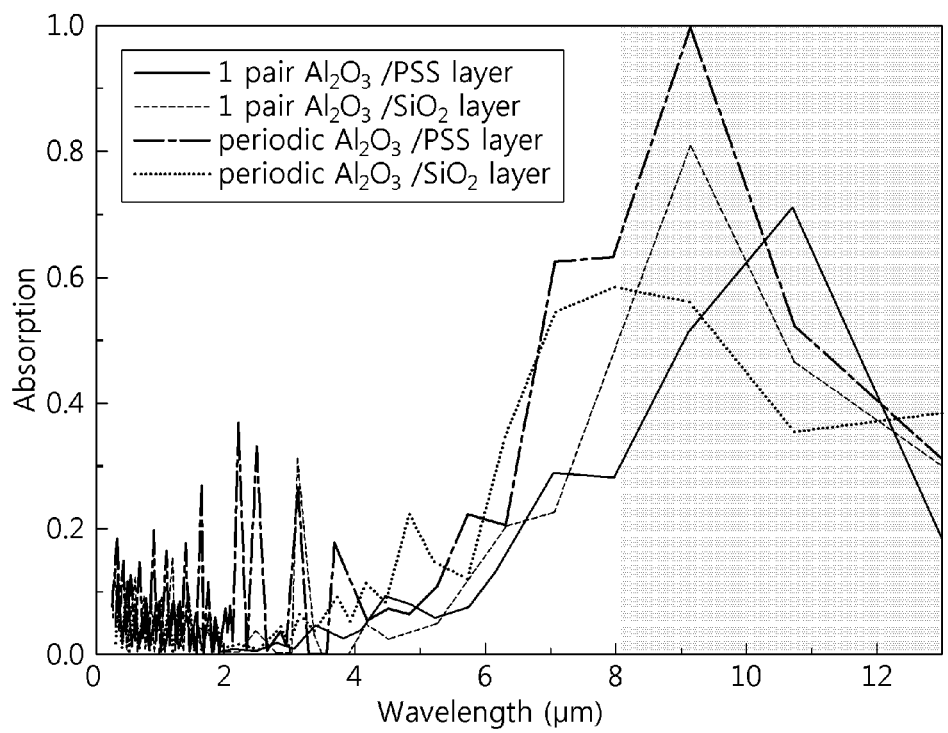
FIG. 5 is a graph showing absorbance according to whether the first radiation layer and the second radiation layer are repeatedly laminated according to examples and comparative examples of the present invention.

Referring to FIG. 5, it can be confirmed that the absorptivity of Example 1-1 (1 pair of $Al_2O_3$/PSS layer) is higher than that of Comparative Example 1-1 (1 pair of $Al_2O_3$/$SiO_2$ layer) with respect to mid-infrared light (yellow region in FIG. 5).

Accordingly, it can be seen that, compared to Comparative Example 1-1 without an uneven pattern, Example 1-1 having an uneven pattern emits mid-infrared light more effectively.

In addition, it can be confirmed that the absorptivity of Example 1-2 (periodic $Al_2O_3$/PSS layer) is higher than that of Comparative Example 1-2 (periodic $Al_2O_3$/$SiO_2$ layer) in a mid-infrared region.

Accordingly, it can be seen that, compared to Comparative Example 1-2 without an uneven pattern, Example 1-2 having an uneven pattern emits mid-infrared light more effectively.

In conclusion, by including an uneven pattern, a radiative cooling device according to an embodiment of the present invention may improve mid-infrared radiation efficiency.

2. Evaluation of Cooling Efficiency of Radiative Cooling Device According to Types of Materials The cooling efficiency of the radiative cooling device of Example 2 was evaluated through simulation, and the results are described below.

Figure 6:
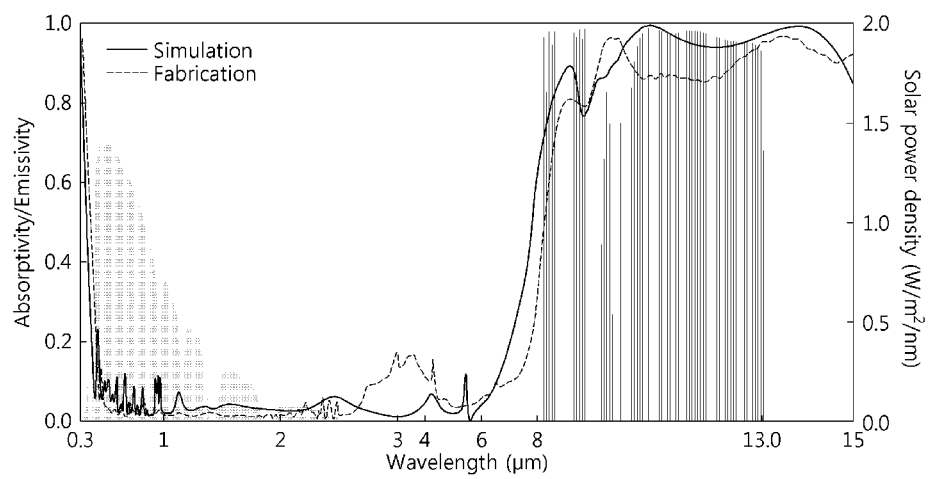
FIG. 6 is a graph showing the absorptivity and emissivity of a radiative cooling device according to Example 2 of the present invention.

FIG. 6 is a graph showing the absorptivity and emissivity of the radiative cooling device according to Example 2 of the present invention.

In this case, the yellow region of FIG. 6 means incident sunlight.

Referring to FIG. 6, simulation results show that the radiative cooling device has a degree of temperature change of −8.18° C. and a cooling efficiency of 81.8 $W/m^2$.

In this case, the degree of temperature change refers to change in temperature after cooling from the initial temperature of a radiative cooling device. When the degree of temperature change is −8.18° C., this means that the temperature of the radiative cooling device is 8.18° C. lower than the initial temperature.

In addition, it can be confirmed that there is no significant difference between the simulation (Simulation) and the emissivity of Example 2 (Fabrication) for average sunlight absorptivity and the mid-infrared region (blue region in FIG. 6).

That is, it can be seen that Example 2 was manufactured in good accordance with the simulation result.

Figure 7:
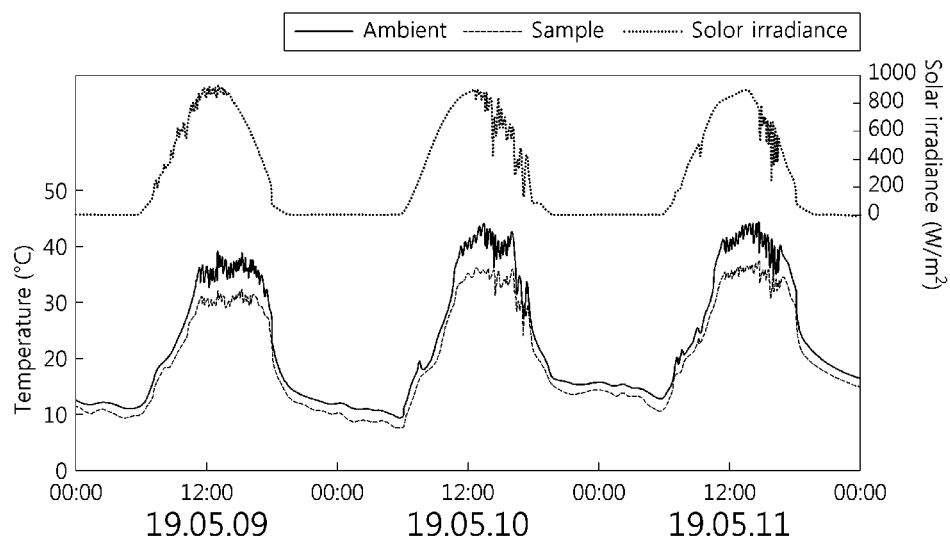
FIG. 7 is a graph showing the temperature of a radiative cooling device according to Example 2 of the present invention during the daytime for each day according to solar radiation quantity.

FIG. 7 is a graph showing the temperature of a radiative cooling device according to Example 2 of the present invention during the daytime for each day according to solar radiation quantity.

Referring to FIG. 7, for Example 2, the temperature of the radiative cooling device was measured for 3 days from midnight on May 9, 2019 to midnight on May 11, 2019.

As a result, it can be confirmed that, in Example 2, temperature rises and falls according to the intensity of sunlight, and the degree of temperature change is −8° C. at maximum during the day and −2° C. at night.

Figure 8:
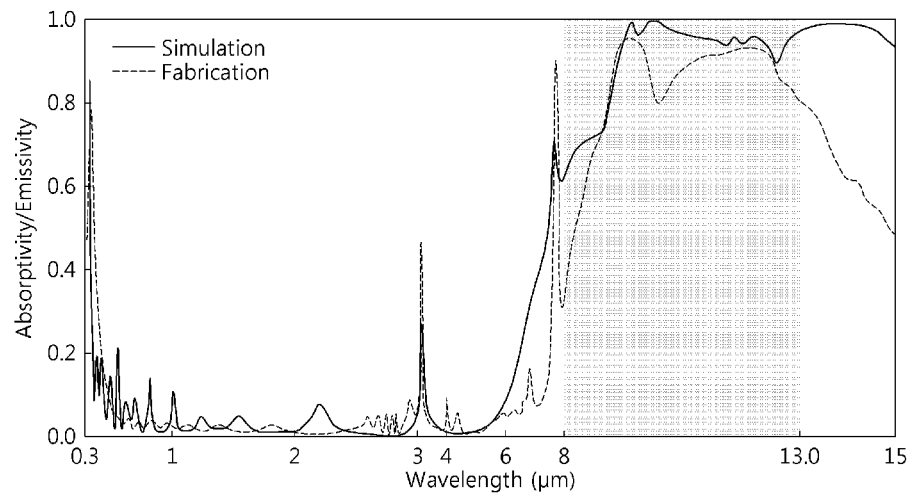
FIG. 8 is a graph showing the absorptivity and emissivity of a radiative cooling device according to Example 3-1 of the present invention.

FIG. 8 is a graph showing the absorptivity and emissivity of a radiative cooling device according to Example 3-1 of the present invention.

Referring to FIG. 8, as a result of simulation, the radiative cooling device of Example 3-1 is predicted to have a degree of temperature change of −9.132° C. and a cooling efficiency of 80.44 $W/m^2$.

As a result of measuring the actual absorptivity for Example 3-1, it can be confirmed that a solar region has a minimum emission rate and a maximum reflectance. It can be seen that the device has a maximum emission rate in a mid-infrared region (blue region in FIG. 8).

Figure 9:
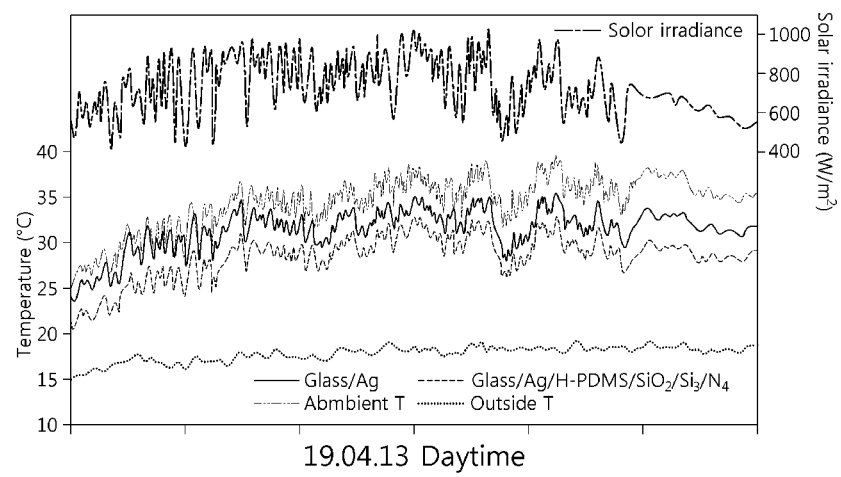
FIG. 9 is a graph showing the external temperature of radiative cooling devices according to Example 3-1 and Comparative Example 2 of the present invention during daytime according to solar radiation quantity.

FIG. 9 is a graph showing the external temperature of radiative cooling devices according to Example 3-1 and Comparative Example 2 of the present invention during daytime according to solar radiation quantity.

Referring to FIG. 9, as a result of observing the temperatures of Example 3-1 and Comparative Example 2 in the daytime (10 am to 4 pm) on Apr. 13, 2019, it can be seen that the degree of temperature change of Comparative Example 2 is −3° C. and the degree of temperature change of Example 3-1 is −5.95° C. compared to the ambient temperature (Ambient T).

At this time, external temperature (Outside T) is lower than the temperatures of Example 3-1 and Comparative Example 2 due to heat loss due to air.

Accordingly, the radiative cooling device of the present invention may have excellent cooling efficiency due to a radiative cooling layer formed of a material capable of emitting mid-infrared light.

Figure 10:
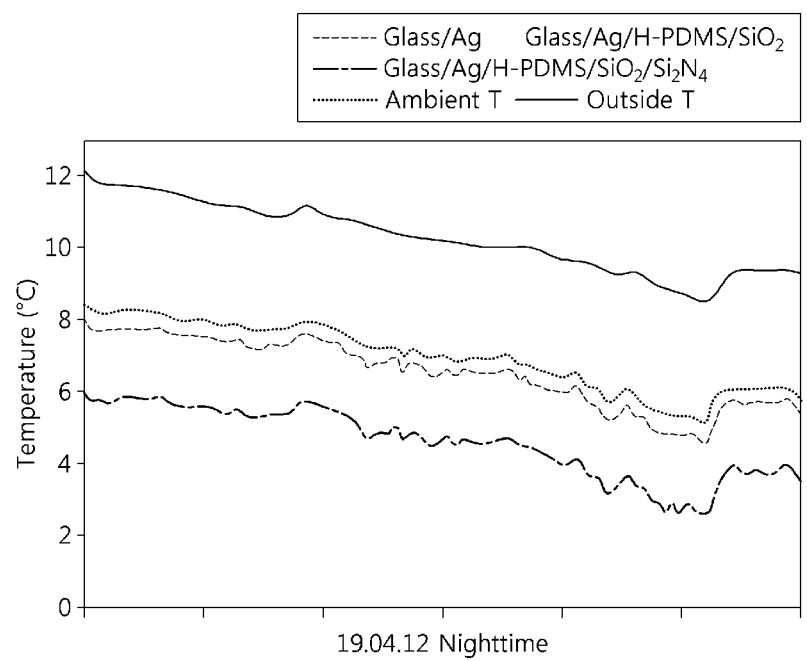
FIG. 10 is a graph showing the temperature of radiative cooling devices according to Example 3-1, Example 3-2, and Comparative Example 2 of the present invention during nighttime.

FIG. 10 is a graph showing the temperature of radiative cooling devices according to Example 3-1, Example 3-2, and Comparative Example 2 of the present invention during nighttime.

Referring to FIG. 10, as a result of observing the temperatures of Example 3-1, Example 3-2, and Comparative Example 2 during the night (10 pm to 4 am) of Apr. 13, 2019, it can be confirmed that, compared to atmospheric temperature (Ambient T), Comparative Example 2 has a degree of temperature change of −0.5° C., and Example 3-1 and Example 3-2 have a degree of temperature change of −2.5° C.

Figure 11:
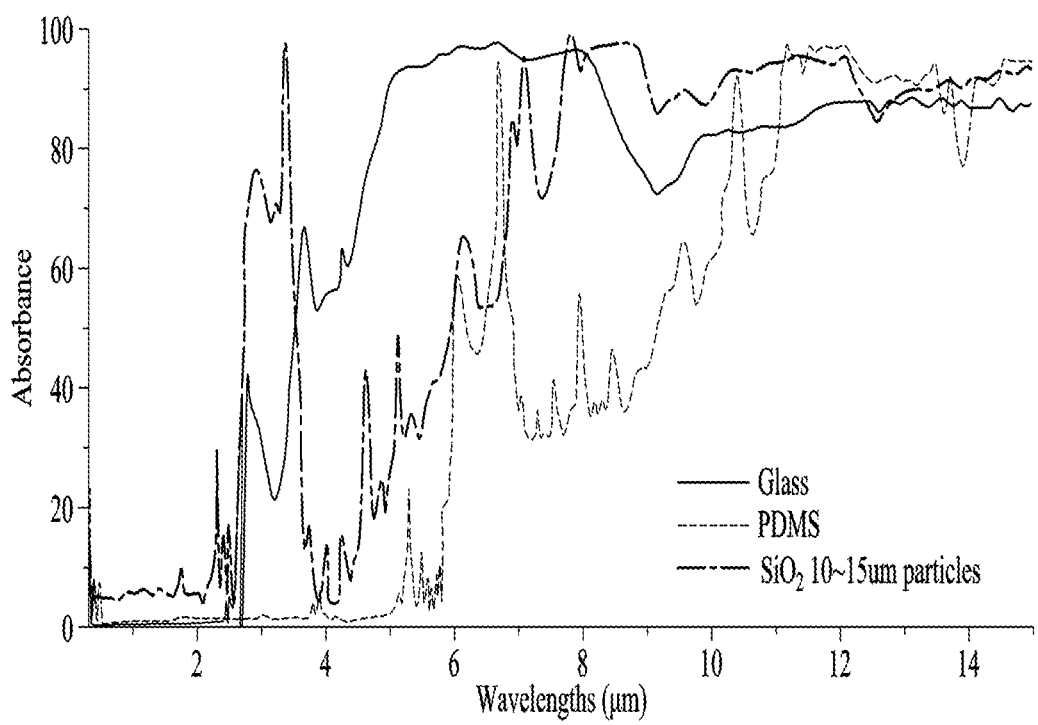
FIG. 11 is a graph showing the absorbance of radiative cooling devices according to Example 4-1, Example 4-2, and Comparative Example 3 of the present invention.

FIG. 11 is a graph showing the absorbance of radiative cooling devices according to Example 4-1, Example 4-2, and Comparative Example 3 of the present invention.

Referring to FIG. 11, it can be confirmed that, compared to Comparative Example 3, Example 4-1 and Example 4-2 exhibit high emissivity in a mid-infrared region.

In particular, it can be seen that Example 4-1 hardly absorbs visible light and exhibits high absorptivity in a long-wavelength region.

Accordingly, Example 4-1 has a degree of temperature change of −9.5° C. and a cooling efficiency of 99.16 W/m².

Figure 12:
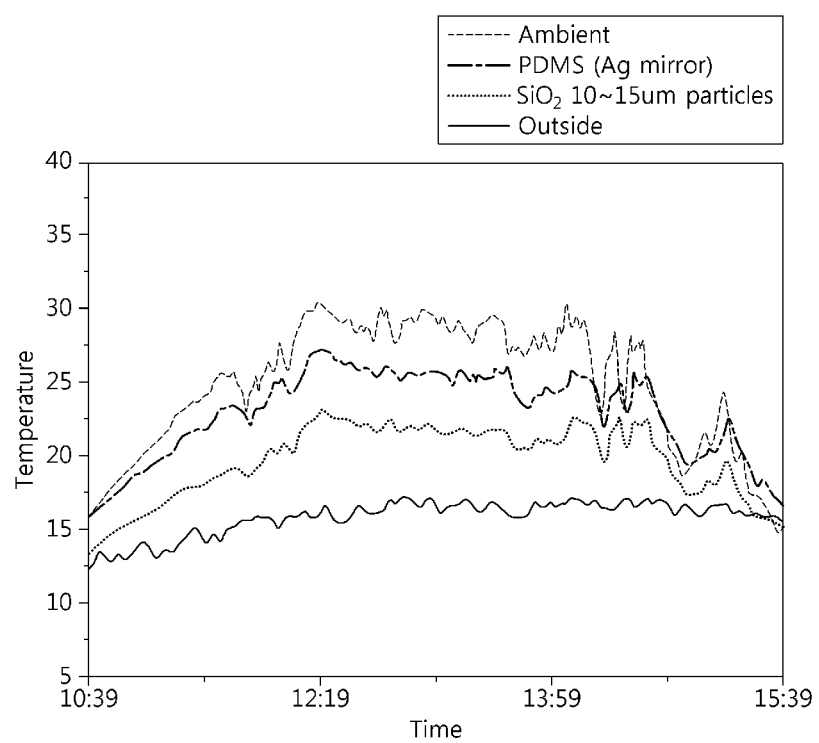
FIG. 12 is a graph showing the temperature and external temperature of radiative cooling devices according to Example 4-1 and Example 4-2 of the present invention during daytime.

FIG. 12 is a graph showing the temperature and external temperature of radiative cooling devices according to Example 4-1, Example 4-2, and Comparative Example 3 of the present invention during daytime.

Referring to FIG. 12, as a result of observing the temperatures of Example 4-1 and Example 4-2 for 5 hours from 10:39 am to 3:39 pm on Apr. 25, 2019, it can be confirmed that the devices have low temperature compared to atmospheric temperature (Ambient).

In particular, it can be confirmed that Example 4-1 has a maximum degree of temperature change of −8° C.

Figure 13:
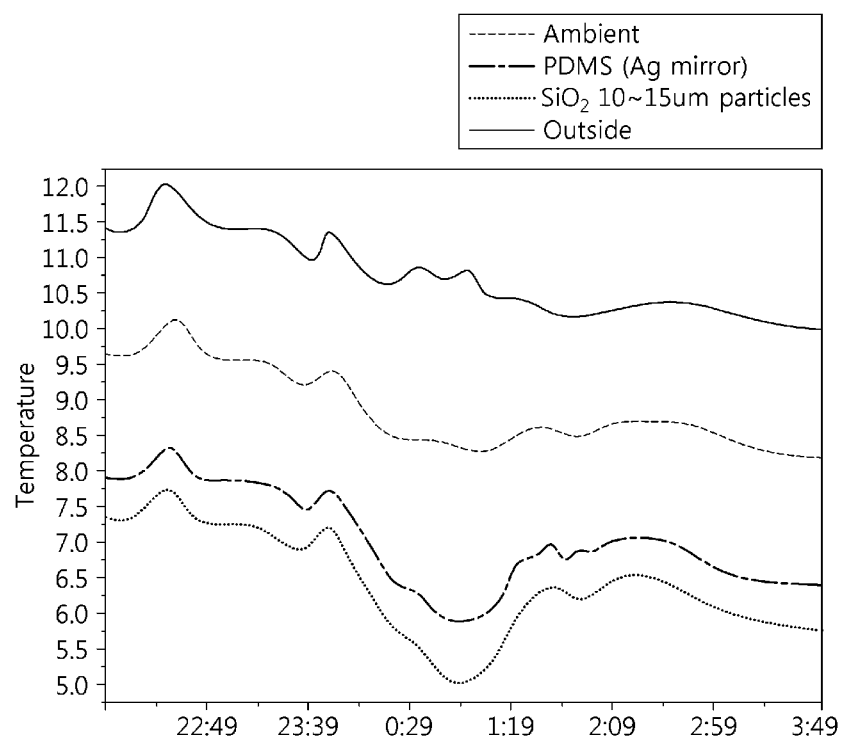
FIG. 13 is a graph showing the temperature and external temperature of radiative cooling devices according to Example 4-1 and Example 4-2 of the present invention during the night.

FIG. 13 is a graph showing the temperature and external temperature of radiative cooling devices according to Example 4-1 and Example 4-2 of the present invention during the night.

Referring to FIG. 13, as a result of observing the temperatures of Example 4-1 and Example 4-2 for 5 hours from 10:49 pm to 3:49 am on Apr. 25, 2019, it can be confirmed that the temperatures of the radiative cooling devices are reduced compared to atmospheric temperature (Ambient).

In particular, it can be confirmed that Example 4-1 has a maximum degree of temperature change of −3° C.

Accordingly, by including a radiative cooling layer formed of fine particles or a polymer capable of emitting mid-infrared light, the radiative cooling device of the present invention may have excellent cooling efficiency during both day and night.

Figure 14A:
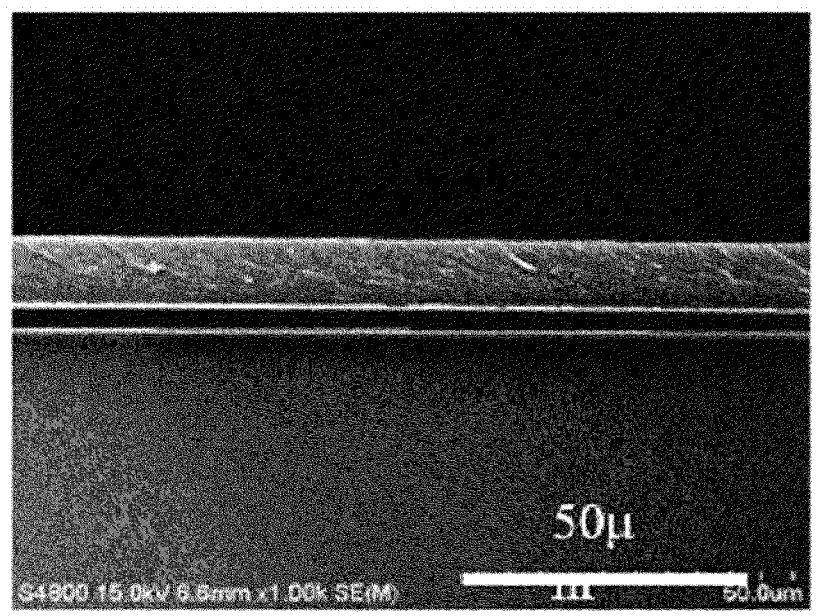
FIGS. 14A to 14C are scanning electron microscope (SEM) images showing the cross section of a radiative cooling device according to Example 5 of the present invention.
Figure 14B:
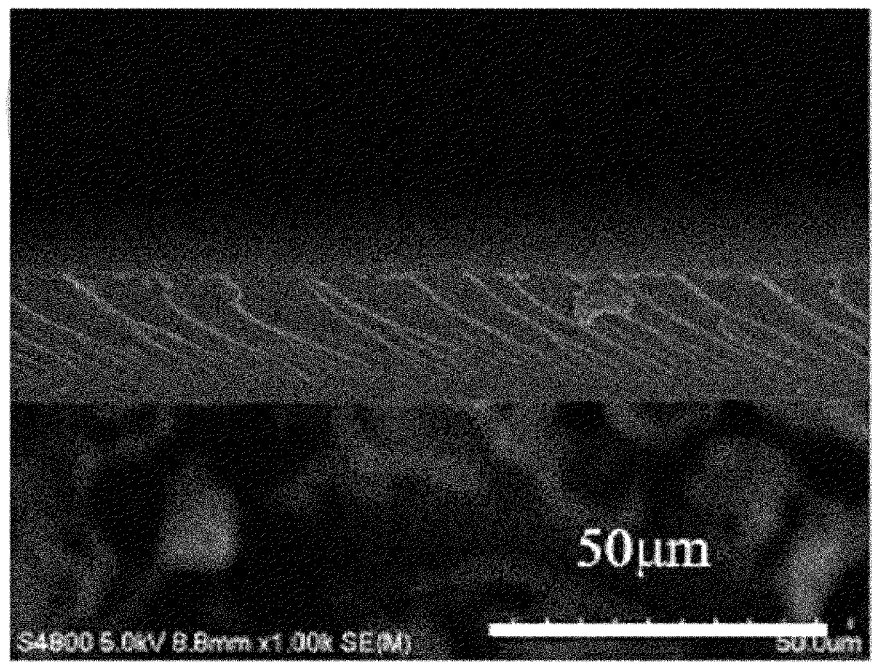
Figure 14C:
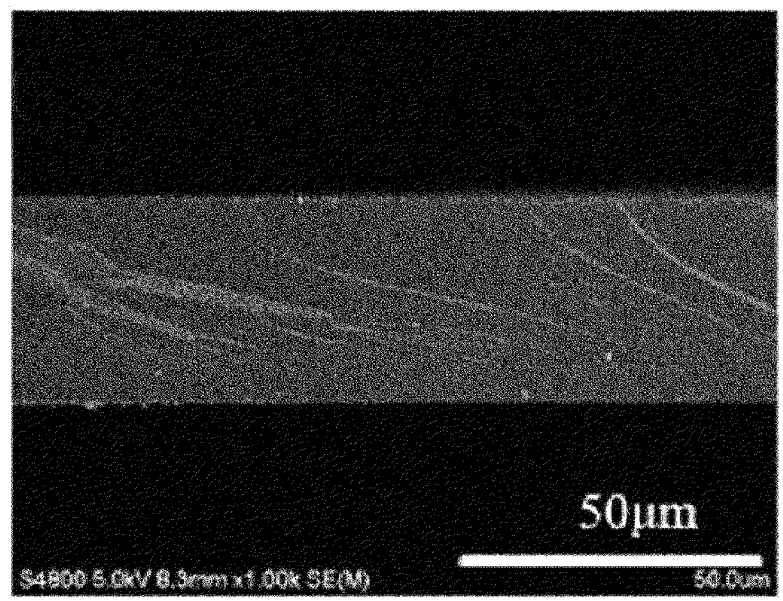

FIGS. 14A to 14C are scanning electron microscope (SEM) images showing the cross section of a radiative cooling device according to Example 5 of the present invention.

Referring to FIGS. 14A to 14C, when the content of DPHA included in the radiative cooling layer of Example 5 is 60% by weight, 80% by weight, or 90% by weight, the thickness of the radiative cooling layer is 10.5 μm, 16.5 μm, or 25.7 μm, respectively. It can be confirmed that the thickness of the radiative cooling layer is proportional to the amount of DPHA.

As the content of DPHA applied on the reflective layer through spin coating increases, viscosity increases. As a result, the thickness of the radiative cooling layer increases even under the same spin coating conditions.

Figure 15:
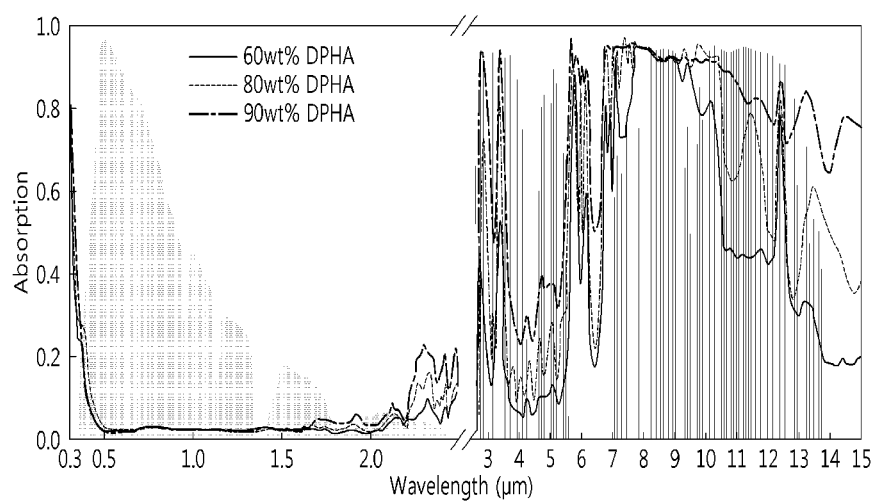
FIG. 15 is a graph showing the absorbance of a radiative cooling device according to Example 5 of the present invention according to the content of DPHA.

FIG. 15 is a graph showing the absorbance of a radiative cooling device according to Example 5 of the present invention according to the content of DPHA.

Referring to FIG. 15, it can be confirmed that, when the content of DPHA included in the radiative cooling layer of Example 5 increases, the device has high emissivity in a wavelength region of 10 μm to 12 μm.

Accordingly, as the content of DPHA included in the radiative cooling layer increases, mid-infrared emissivity increases in a mid-infrared region, thereby improving the cooling efficiency of the radiative cooling device.

Figure 16:
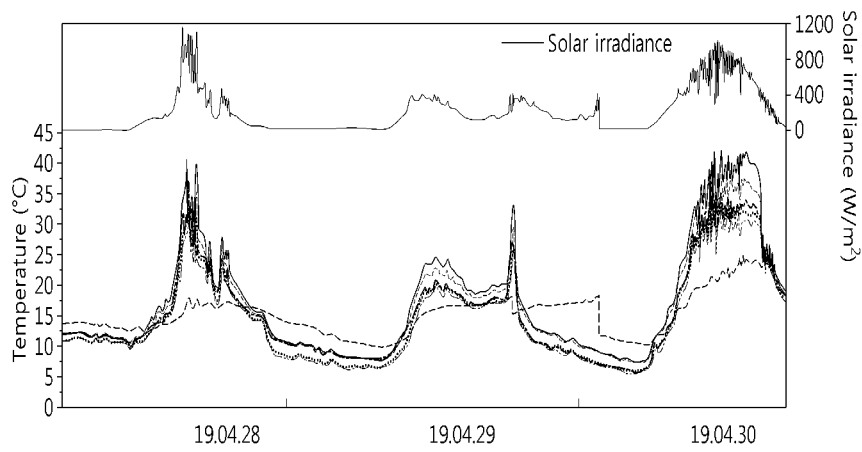
FIG. 16 is a graph showing the temperature of a radiative cooling device according to Example 5 of the present invention by observation period according to solar radiation quantity.

FIG. 16 is a graph showing the temperature of a radiative cooling device according to Example 5 of the present invention by observation period according to solar radiation quantity.

Referring to FIG. 16, as a result of observing the temperature of Example 5 for 3 days from Apr. 28, 2019 to Apr. 30, 2019, it can be confirmed that, as the content of DPHA increases, mid-infrared emissivity increases and the degree of temperature change increases.

In particular, it can be confirmed that, in Example 5, when the content of DPHA is 90% by weight, the degree of temperature change is −10.1° C.

Accordingly, by including a radiative cooling layer formed of a polymer having resonance effect due to chemical bonding of molecules, the radiative cooling device of the present invention may have excellent radiative cooling efficiency due to high mid-infrared emissivity.

Figure 17:
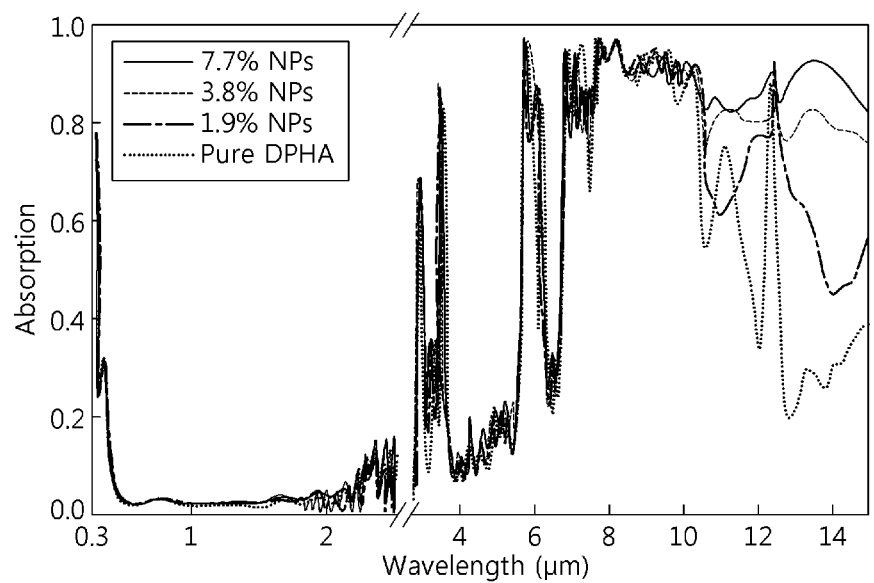
FIG. 17 is a graph showing the absorptivity of a radiative cooling device according to Example 6-1 of the present invention according to the content of fine particles.

FIG. 17 is a graph showing the absorptivity of a radiative cooling device according to Example 6-1 of the present invention according to the content of fine particles.

Referring to FIG. 17, it can be confirmed that, as the content of alumina fine particles of Example 6-1 increases, emissivity in a mid-infrared region increases.

Figure 18:
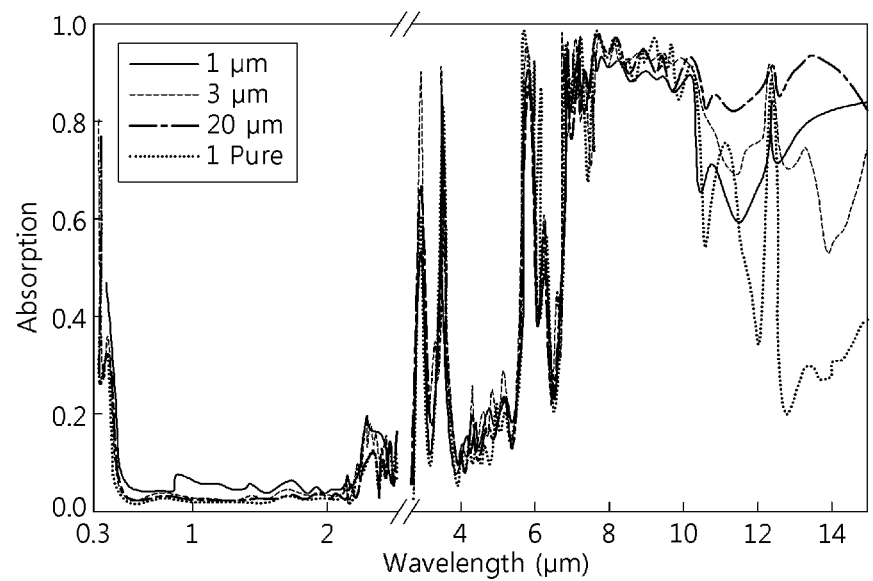
FIG. 18 is a graph showing the absorptivity of a radiative cooling device according to Example 6-2 of the present invention according to the diameter of fine particles.

FIG. 18 is a graph showing the absorptivity of a radiative cooling device according to Example 6-2 of the present invention according to the diameter of fine particles.

Referring to 18, it can be confirmed that, as the diameter of alumina fine particles of Example 6-2 increases, emissivity in a mid-infrared region decreases.

Accordingly, it can be seen that, when the radiative cooling device according to an embodiment of the present invention contains nanometer-scale fine particles in a high content, the radiative cooling device has excellent cooling efficiency.

Figure 19:
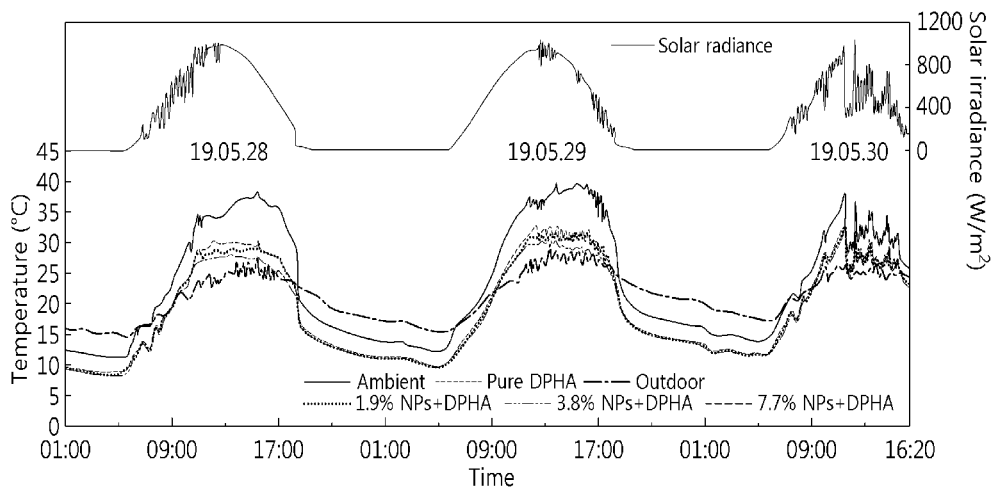
FIG. 19 is a graph showing the temperature of a radiative cooling device according to Example 5 of the present invention according to the content of fine particles according to solar radiation quantity.

FIG. 19 is a graph showing the temperature of a radiative cooling device according to Example 5 of the present invention according to the content of fine particles according to solar radiation quantity.

Referring to FIG. 19, as a result of observing the temperature of Example 6-1 from May 28, 2019 to May 30, 2019, it can be confirmed that, as the content of alumina fine particles increases, mid-infrared emissivity increases and cooling efficiency is improved.

In particular, it can be confirmed that, when the content of alumina fine particles is 7.7% by weight, the maximum degree of temperature change of Example 6-1 is −11.9° C.

Accordingly, by including fine particles capable of emitting mid-infrared light, the mid-infrared emissivity of the radiative cooling device according to an embodiment of the present invention may be increased, thereby increasing radiative cooling efficiency.

3. Evaluation of Efficiency of Radiative Cooling Device According to Presence or Absence of Uneven Pattern FIG. 20 is a graph showing absorptivity according to the presence or absence of an uneven pattern according to Example 7 and Comparative Example 4 of the present invention.

The first radiation layers of Example 7 and Comparative Example 4 are formed of oxide semiconductors having the same volume.

Figure 20:
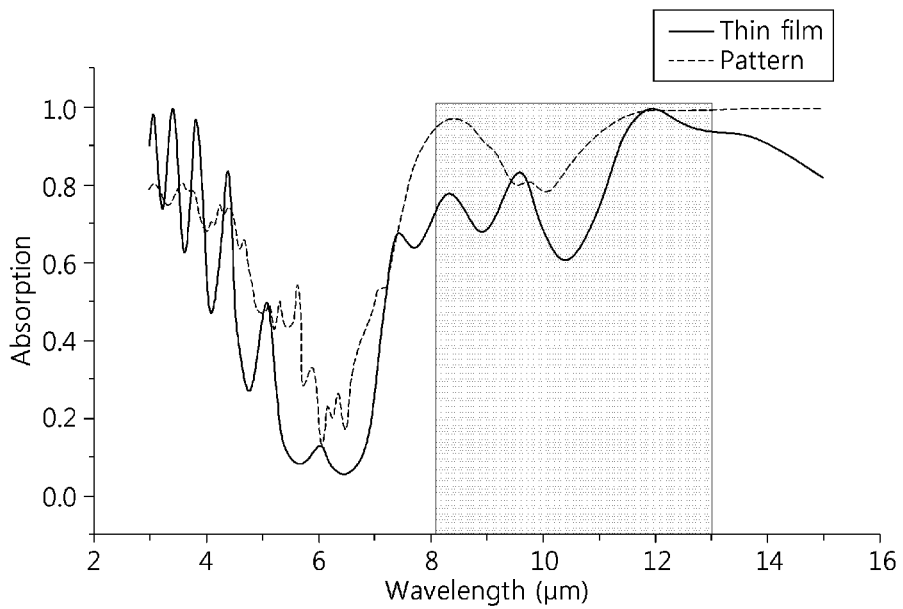
FIG. 20 is a graph showing absorptivity according to the presence or absence of an uneven pattern according to Example 7 and Comparative Example 4 of the present invention.

Referring to FIG. 20, it can be confirmed that Example 7 (Pattern) has higher absorptivity than Comparative Example 4 (Thin film) in the red region corresponding to a mid-infrared region.

That is, it can be confirmed that, since the first radiation layer of Example 7 includes an uneven pattern, absorption of mid-infrared light is increased by resonance of an electric field and a magnetic field at a specific wavelength.

Accordingly, when the uneven pattern is formed at the micrometer scale, the radiative cooling device according to an embodiment of the present invention may selectively increase mid-infrared light absorptivity in a wavelength corresponding to a mid-infrared region, and thus radiation of mid-infrared light may be promoted, thereby achieving excellent cooling effect.

4. Evaluation of Efficiency of Radiative Cooling Device According to Presence or Absence of Coating Layers Having Different Refractive Indexes FIG. 21 is a graph showing the mid-infrared emissivity of radiative cooling devices according to Example 8, Comparative Example 5-1, and Comparative Example 5-2 of the present invention.

Figure 21:
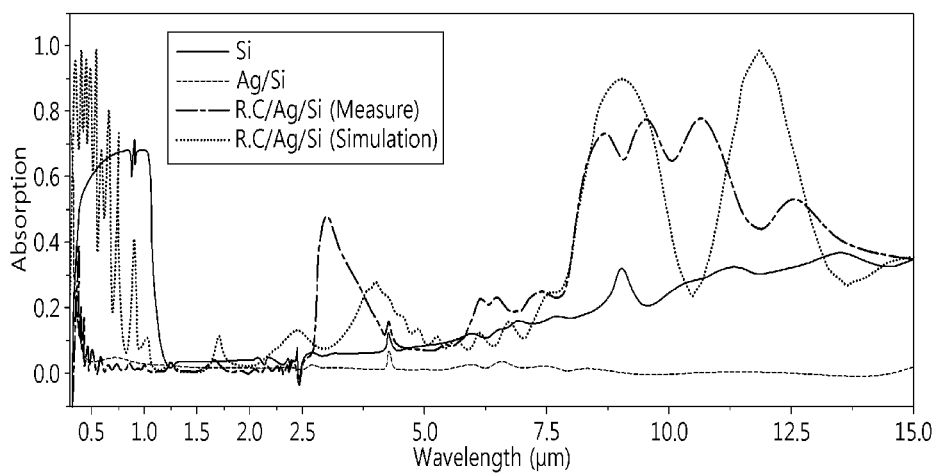
FIG. 21 is a graph showing the mid-infrared emissivity of radiative cooling devices according to Example 8, Comparative Example 5-1, and Comparative Example 5-2 of the present invention.

Referring to FIG. 21, it can be confirmed that, compared to Comparative Example 5-1 (Ag/Si) and Comparative Example 5-2 (Si), Example 8 (R. C. (radiative cooling)/Ag/Si) exhibits increased emissivity in a wavelength range of 8 μm to 13 μm corresponding to a mid-infrared region.

Figure 22A:
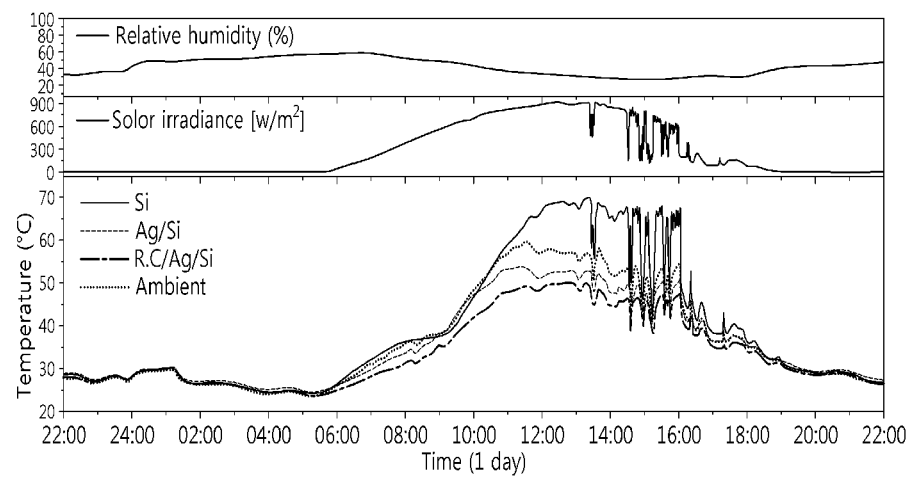
FIGS. 22A to 22C are graphs showing the temperature and the temperature change of radiative cooling devices according to Example 8, Comparative Example 5-1, and Comparative Example 5-2 of the present invention over time.
Figure 22B:
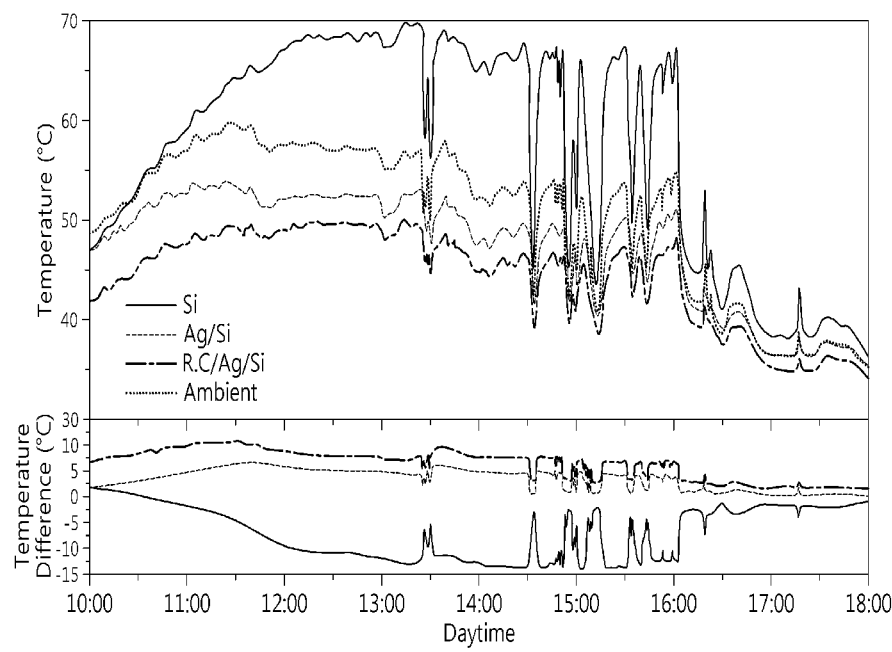
Figure 22C:
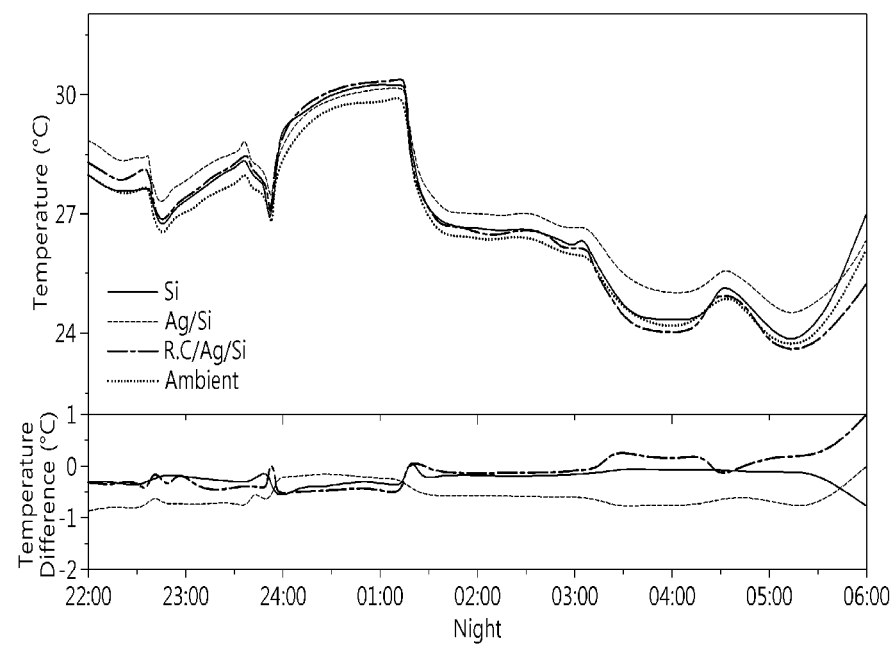

FIGS. 22A to 22C are graphs showing the temperature and the temperature change of radiative cooling devices according to Example 8, Comparative Example 5-1, and Comparative Example 5-2 of the present invention over time.

FIG. 22A shows the result of observing the temperature and the degree of temperature change of the radiative cooling devices of Example 8, Comparative Example 5-1, and Comparative Example 5-2 during the day, FIG. 22B shows the result of observing the temperature and the degree of temperature change of the radiative cooling devices of Example 8, Comparative Example 5-1, and Comparative Example 5-2 during the daytime (10:00 to 18:00), and FIG. 22C shows the result of observing the temperature and the degree of temperature change of the radiative cooling devices of Example 8, Comparative Example 5-1, and Comparative Example 5-2 during the night (22:00 to 06:00).

Referring to FIG. 22A, it can be confirmed that, compared to Comparative Example 5-1 (Ag/Si) and Comparative Example 5-2 (Si), Example 8 (R. C/Ag/Si) exhibits low temperature. In addition, considering that Example 8 exhibits lower temperature than external temperature (Ambient), Example 8 has excellent cooling efficiency.

Referring to FIGS. 22B and 22C, it can be confirmed that, compared to Comparative Example 5-1 (Ag/Si) and Comparative Example 5-2 (Si), Example 8 (R. C/Ag/Si) exhibits low temperature in both daytime and nighttime.

In particular, it can be confirmed that, considering that the degree of temperature change of Example 8 (R. C./Ag/Si) is higher than that of Comparative Example 5-1 (Ag/Si) and Comparative Example 5-2 (Si), Example 8 has excellent cooling efficiency.

Accordingly, by including coating layers including materials having different refractive indexes, the radiative cooling device according to another embodiment of the present invention may have excellent cooling efficiency.

A white radiative cooling device according to an embodiment of the present invention absorbs mid-infrared light and emits the mid-infrared light as heat while reflecting or scattering visible light. The white radiative cooling device is formed on the surface of an object. The white radiative cooling device serves to lower the temperature of the object located under the white radiative cooling device below external temperature.

For example, when the white radiative cooling device according to an embodiment of the present invention is provided on the surface of an automobile, the white radiative cooling device emits mid-infrared light while reflecting or scattering visible light so that the temperature of the white radiative cooling device decreases. Accordingly, the temperature of the automobile frame becomes lower than external temperature, or the temperature inside the automobile becomes lower than external temperature.

In this case, the object is an object equipped with the white radiative cooling device, and may be an automobile or a building such as an apartment, a shopping mall, or an office building, and any objects that may be equipped with the white radiative cooling device according to an embodiment of the present invention may be used without particular limitation.

In this case, external temperature means atmospheric temperature, and may be the external temperature of the white radiative cooling device according to an embodiment of the present invention.

The white radiative cooling device according to an embodiment of the present invention may include fine particles or polymers having different refractive indexes to reflect and scatter visible light. Accordingly, the white radiative cooling device may appear white.

Hereinafter, the configuration of the white radiative cooling device according to an embodiment of the present invention will be described with reference to drawings.

Figure 23A:
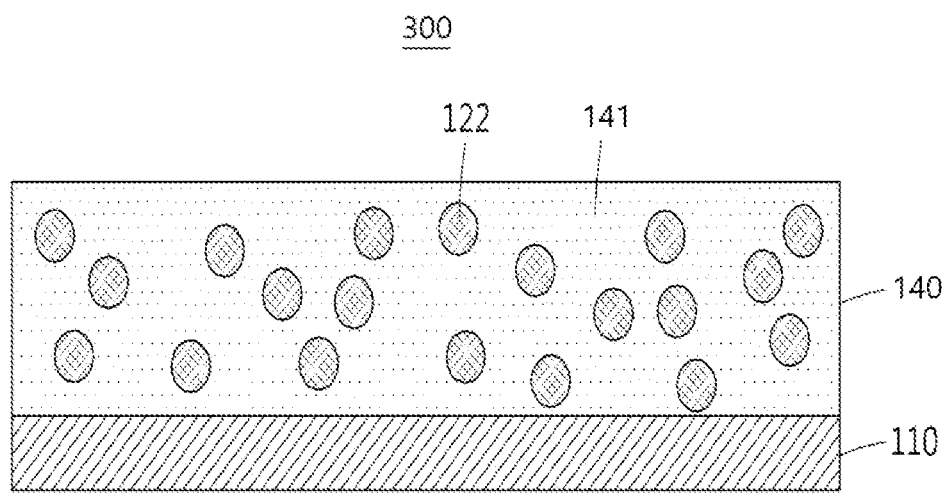
FIGS. 23A to 23C each show a cross-sectional view of a white radiative cooling device according to an embodiment of the present invention.
Figure 23B:
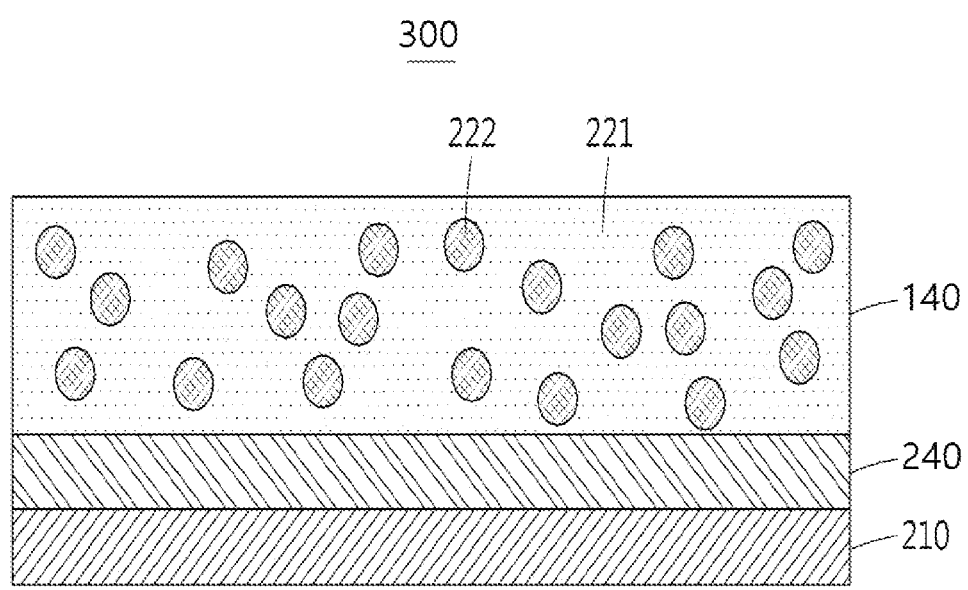
Figure 23C:
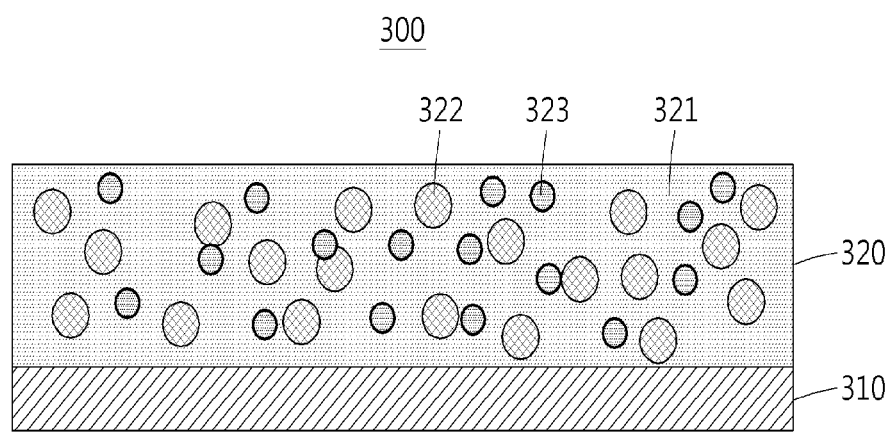

FIGS. 23A to 23C each show a cross-sectional view of a white radiative cooling device according to an embodiment of the present invention.

Referring to FIG. 23A, the white radiative cooling device 300 according to the first embodiment of the present invention includes the substrate 110; and a white radiative cooling layer 140 formed on the substrate 110 and including a polymer matrix 141 that absorbs sunlight having a wavelength corresponding to a mid-infrared region and emits the sunlight as heat and fine particles 122 that reflect and scatter sunlight having a wavelength corresponding to a visible region, wherein the fine particles 122 are embedded in the polymer matrix 141.

The substrate 110 may be formed of any one of a flexible polymer film, glass, quartz, silicon wafer, and a metal material, without being limited thereto.

For example, the substrate 110 may be a polymer film formed of any one of polyester-based resins such as polyethylene naphthalate (PEN), acetate-based resins, polyethersulfone-based resins, polycarbonate-based resins, polyamide-based resins, polyimide-based resins, polyolefin-based resins, (meth)acrylic resins, polyvinyl chloride-based resins, polyvinylidene chloride-based resins, polystyrene-based resins, polyvinyl alcohol-based resins, polyarylate-based resins, and polyphenylene sulfide-based resins, without being limited thereto.

The white radiative cooling layer 140 may be formed on the substrate 110. In the white radiative cooling layer 140, the fine particles 122 that reflect and scatter visible light may be embedded in the polymer matrix 141 that absorbs mid-infrared light or long-wavelength infrared light and emits the light as heat. Thus, the temperature of an object may be lower than external temperature by the white radiative cooling device 300 according to the first embodiment of the present invention.

In general, since objects on the earth have a surface temperature of several tens of degrees C., these objects emit mid-infrared light with a wavelength of 8 μm to 13 μm.

Such mid-infrared radiation may lower the temperature of an object, and the white radiative cooling layer 140 includes the polymer matrix 141 made of a material capable of effectively emitting mid-infrared light of the atmospheric window corresponding to a wavelength range of 8 µm to 13 µm, thereby reducing the temperature of the white radiative cooling device 300 according to the first embodiment of the present invention. As a result, the temperature of the object may be kept lower than external temperature.

The polymer matrix 141 may absorb sunlight having a wavelength corresponding to a mid-infrared region and emit the sunlight as heat.

According to an embodiment, the polymer matrix 141 may include an acrylic polymer.

The acrylic polymer has C—O stretching vibration, and thus has high emissivity in a wavelength corresponding to a mid-infrared region.

For example, the polymer matrix 141 may include at least one of polydimethylsiloxane (PDMS), polymethyl methacrylate (PMMA), and dipentaerythritol penta/hexa acrylate (DPHA), without being limited thereto.

In particular, DPHA has high emissivity in a wavelength corresponding to a mid-infrared region due to C—O stretching vibration and C=C bending vibration.

According to an embodiment, the polymer matrix 141 may be formed of polyvinylidene fluoride (PVDF) or polyurethane acrylate (PUA).

In the white radiative cooling layer 140, the fine particles 122 including a metal oxide or a polymer may be embedded in the polymer matrix 141.

The fine particles 122 including the metal oxide may reflect and scatter sunlight having a wavelength corresponding to a visible region. Due to reflection and scattering of visible light by the fine particles 122, the white radiative cooling device 300 according to the first embodiment of the present invention may appear white.

Specifically, the fine particles 122 including a metal oxide that does not absorb visible light may reflect visible light in various directions (diffusive reflection). Thus, the white radiative cooling device 300 according to the first embodiment of the present invention may appear white without having a mirror-like appearance like a conventional radiative cooling device.

In addition, when the fine particles 122 include a polymer, the polymer matrix 141 and the fine particles 122 including the polymer may have different refractive indexes. Due to different refractive indexes, the white radiative cooling device 300 according to the first embodiment of the present invention may promote scattering and reflection of visible light.

According to an embodiment, the polymer matrix 141 and the fine particles 122 may be formed of materials having a refractive index of 1.4 to 1.7. As difference in refractive indexes increases, scattering or reflection of visible light may be promoted.

According to an embodiment, the polymer may include at least one of polyvinylidene fluoride (PVDF) and polyurethane acrylate (PUA).

For example, in the white radiative cooling layer 140, the fine particles 122 including PUA (refractive index of about 1.55) may be embedded in the polymer matrix 141 made of PVDF (refractive index of about 1.426).

As another example, in the white radiative cooling layer 140, the fine particles 122 including PVDF may be embedded in the polymer matrix 141 made of PUA.

When the polymer matrix 141 and the fine particles 122 including a polymer have different refractive indexes, when visible light is incident on the interface between the fine particles 122 and the polymer matrix 141, visible light may be scattered and reflected, thereby improving cooling performance without energy consumption.

According to an embodiment, based on the total weight of the polymer matrix 141, 1% by weight to 50% by weight of the fine particles 122 may be embedded in the polymer matrix 141.

According to an embodiment, the metal oxide may include at least one of titanium dioxide ($TiO_2$), zirconium oxide ($ZrO_2$), alumina ($Al_2O_3$), zinc oxide (ZnO), silicon oxide ($SiO_2$), and silicon nitride ($Si_3N_4$), without being limited thereto.

As the diameter of the fine particles 122 decreases, reflectance and scattering rate with respect to visible light may be increased.

According to an embodiment, the fine particles 122 may have a diameter of 10 nm to 20 µm.

When the fine particles 122 have a nanometer-scale diameter, all incident sunlight may be reflected or scattered.

When the diameter of the fine particles 122 exceeds 3 µm, absorption of light corresponding to a long-wavelength region is increased, so that heat emission may be improved.

Preferably, the fine particles 122 having a nanometer-scale diameter may have higher visible light reflectance (or scattering rate) than the fine particles 122 having a micrometer-scale diameter.

By including the white radiative cooling layer 140 including the polymer matrix 141 that emits mid-infrared light or long-wavelength infrared light and the fine particles 122 that reflect and scatter visible light, the white radiative cooling device 300 according to the first embodiment of the present invention may have excellent cooling performance.

In addition, the white radiative cooling device 300 according to the first embodiment of the present invention may appear white due to the fine particles 122 that reflect and scatter visible light, thereby improving aesthetics.

Referring to FIG. 23b, a white radiative cooling device 300 according to the second embodiment of the present invention may further include, on the lower surface of a white radiative cooling layer 140, a reflection enhancement layer 240 for additionally reflecting sunlight having a wavelength corresponding to a visible region.

Accordingly, the white radiative cooling device 300 according to the second embodiment of the present invention may include a substrate 210, the reflection enhancement layer 240, and the white radiative cooling layer 140 including fine particles 222 embedded in a polymer matrix 221.

In this case, the white radiative cooling device 300 according to the second embodiment of the present invention includes the components of the white radiative cooling device 300 according to the first embodiment, and thus repeated description thereof will be omitted.

The reflection enhancement layer 240 may additionally reflect ultraviolet light, visible light, and near-infrared light of sunlight to prevent the temperature of the white radiative cooling device 300 according to the second embodiment of the present invention from being increased by sunlight.

The reflection enhancement layer 240 may be formed of a material capable of effectively reflecting sunlight, and in particular, is preferably formed of a material having a reflectance of 90% or more with respect to visible light.

The reflection enhancement layer 240 may be a layer formed by depositing a metal material on the substrate 210.

According to an embodiment, the reflection enhancement layer 240 may be formed by depositing a metal material on the substrate 210 using any one method of sputtering, atomic layer deposition (ALD), chemical vapor deposition (CVD), thermal evaporation, co-evaporation, plasma enhanced chemical vapor deposition (PECVD), e-beam evaporation, radio frequency (RF) sputtering, magnetron sputtering, vacuum deposition, and chemical vapor deposition.

According to an embodiment, the reflection enhancement layer 240 may be formed of at least one metal material of silver (Ag), aluminum (Al), and platinum (Pt), without being limited thereto.

According to an embodiment, the reflection enhancement layer 240 may be formed of a commercially available solar reflective film such as a Solar mirror film manufactured by 3M.

According to an embodiment, in the white radiative cooling device 300 according to the second embodiment of the present invention, the reflection enhancement layer 240 and the white radiative cooling layer 140 may be repeatedly formed.

Specifically, in the white radiative cooling device 300 according to the second embodiment of the present invention, the reflection enhancement layer 240 and the white radiative cooling layer 140 may be repeatedly laminated on the substrate 210 in the order of the reflection enhancement layer 230-the white radiative cooling layer 140 the reflection enhancement layer 230 the white radiative cooling layer 140 . . . .

Referring to FIG. 23C, in a white radiative cooling device 300 according to the third embodiment of the present invention, fluorescent particles 323 for emitting fluorescence may be further embedded in a white radiative cooling layer 320.

Accordingly, the white radiative cooling device 300 according to the third embodiment of the present invention may include a substrate 310; and the white radiative cooling layer 320 formed on the substrate 310 and including a polymer matrix 321 that absorbs mid-infrared light and emits the light as heat, fine particles 322 that reflect and scatter sunlight having a wavelength corresponding to a visible region, and the fluorescent particles 323 for emitting fluorescence, wherein the fine particles 322 and the fluorescent particles 323 are embedded in the polymer matrix 321.

The white radiative cooling device 300 according to the third embodiment of the present invention includes all components of the white radiative cooling device 300 according to the first embodiment or the second embodiment, and thus repeated description thereof will be omitted.

The fluorescent particles 323 included in the white radiative cooling layer 320 serve to absorb sunlight and emit visible light. According to an embodiment, at least one color of visible light may be emitted.

Accordingly, due to color mixing by the fluorescent particles 323 having at least one color, the white radiative cooling device 300 according to the third embodiment of the present invention may appear a variety of colors in addition to white.

According to an embodiment, the fluorescent particles 323 may be made of manganese (Mn) emitting red fluorescence and antimony (Sb) emitting blue fluorescence.

According to an embodiment, the fluorescent particles 323 may be made of a lutetium aluminum garnet (LuAG), a yttrium aluminum garnet (YAG), a nitride, a sulfide, a silicate, or a mixture thereof.

According to an embodiment, in the white radiative cooling device 300 according to the third embodiment of the present invention, the fine particles 322 and a coloring agent 323 may be contained in the polymer matrix 321.

The coloring agent 323 may include metamaterials or dyes, without being limited thereto.

Accordingly, by further including the fluorescent particles 323, the white radiative cooling device 300 according to the third embodiment of the present invention may appear various colors without having a mirror-like appearance, thereby improving aesthetics.

Hereinafter, the white radiative cooling devices were manufactured according to Examples below, and the properties of the white radiative cooling devices were evaluated. Based on the evaluation results, the properties and effects of the white radiative cooling device of the present invention were demonstrated.

Example 1-1

Based on a total weight of PDMS as a polymer, 30% by weight of zinc oxide (ZnO) particles having a diameter of 20 nm as fine particles was mixed with PDMS to prepare a mixed solution.

Then, a glass substrate was coated with silver (Ag) using an e-beam evaporator to form a reflection enhancement layer.

Then, the reflection enhancement layer was spin-coated with the mixed solution to manufacture a white radiative cooling device.

Example 1-2

A white radiative cooling device was manufactured in the same manner as in Example 1-1, except that 50% by weight of zinc oxide particles was mixed.

Example 2-1

Based on a total weight of PDMS as a polymer, 1.9% by weight of alumina ($Al_2O_3$) particles having a diameter of 20 nm as fine particles was mixed with PDMS to prepare a mixed solution.

Then, a glass substrate was coated with silver (Ag) using an e-beam evaporator to form a reflection enhancement layer.

Then, the reflection enhancement layer was spin-coated with the mixed solution to manufacture a white radiative cooling device.

Example 2-2

A white radiative cooling device was manufactured in the same manner as in Example 1-1, except that 3.8% by weight of alumina particles was mixed based on a total weight of DPHA to prepare a mixed solution.

Example 2-3

A white radiative cooling device was manufactured in the same manner as in Example 1-1, except that 7.7% by weight of alumina particles was mixed based on a total weight of DPHA to prepare a mixed solution.

Comparative Example 1

A glass substrate was coated with silver (Ag) using an e-beam evaporator to form a reflective layer made of silver (Ag), and then the reflective layer was spin-coated with DPHA to manufacture a radiative cooling device.

Example 3

Based on a total weight of PUA as a polymer, 33% by weight of PVDF particles having a diameter of 20 nm as fine particles was mixed to prepare a mixed solution.

A glass substrate was spin-coated with the mixed solution to manufacture a white radiative cooling device.

Comparative Example 2-1

A glass substrate was spin-coated with PUA to manufacture a radiative cooling device.

Comparative Example 2-2

Silver substrate.

Characteristics Evaluation

1. White Radiative Cooling Device Including Metal Oxide Fine Particles

Figure 24A:
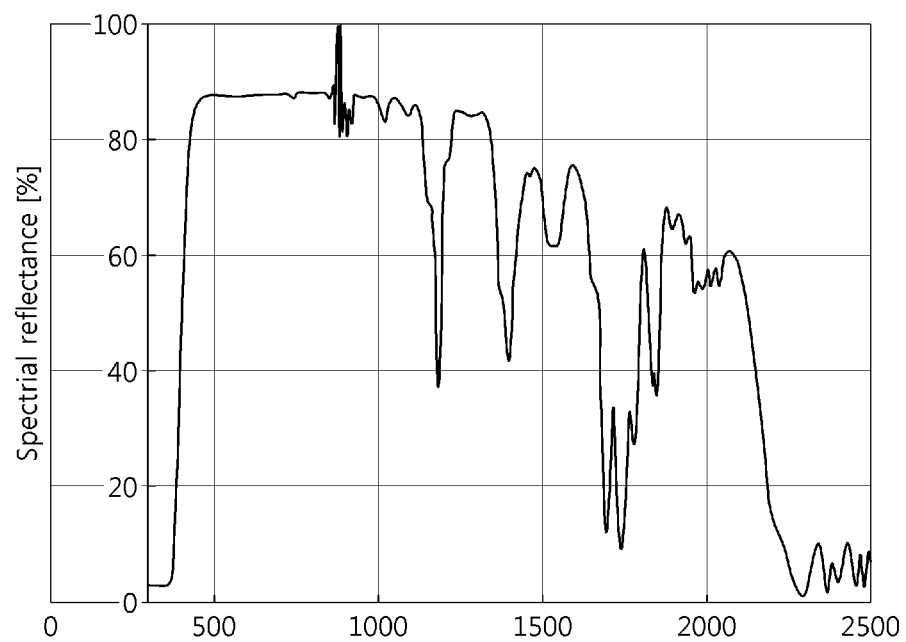
FIGS. 24A and 24B are graphs showing the absorptivity of a white radiative cooling device according to an embodiment of the present invention according to the content of fine particles.
Figure 24B:
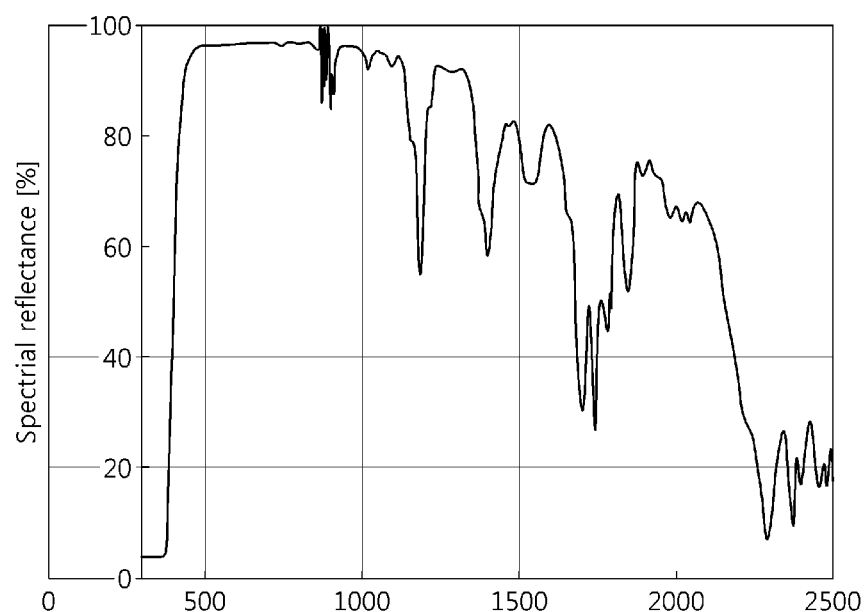

FIGS. 24A and 24B are graphs showing the absorptivity of a white radiative cooling device according to an embodiment of the present invention according to the content of fine particles.

Referring to FIGS. 24A and 24B, it can be confirmed that Example 1-1 (Sample 1) and Example 1-2 have high reflectance with respect to visible light.

In addition, as a result of measuring the reflectance of Example 1-1 and Example 1-2, it can be confirmed that Example 1-2 with a higher content of zinc oxide particles has higher reflectance with respect to visible light than Example 1-1.

That is, as the content of fine particles increases, the transmittance of the white radiative cooling device according to an embodiment of the present invention with respect to visible light decreases, that is the reflectance of the white radiative cooling device increases.

Figure 25:
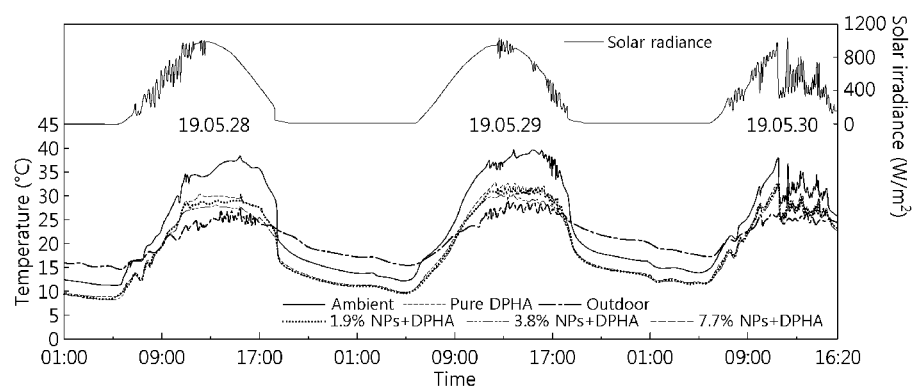
FIG. 25 is a graph showing the temperature of a white radiative cooling device including fine particles according to an embodiment of the present invention over time.

FIG. 25 is a graph showing the temperature of a white radiative cooling device including fine particles according to an embodiment of the present invention over time.

Referring to FIG. 25, in sunny weather on May 28, 2019, Example 2-3 exhibits−11.9° C., Example 2-2 exhibits−11.3° C., Example 2-1 exhibits−9.2° C., and Comparative Example 1 exhibits−8.8° C.

In addition, in sunny weather on May 29, 2019, Example 2-3 exhibits−11.6° C., Example 2-2 exhibits−11.1° C., Example 2-1 exhibits−9.21° C., and Comparative Example 1 exhibits−8.7° C.

In addition, in cloudy weather on May 30, 2019, Example 2-3 exhibits−7.2° C., Example 2-2 exhibits−6.6° C., Example 2-1 exhibits−5.9° C., and Comparative Example 1 exhibits−5.4° C.

That is, the degree of temperature change decreases in the order of Example 2-3, Example 2-2, Example 2-1, and Comparative Example 1. Accordingly, as the content of fine particles increases, mid-infrared emissivity and the reflectance/scattering rate of visible light are increased, thereby improving the cooling efficiency of a white radiative cooling device.

Figure 26A:
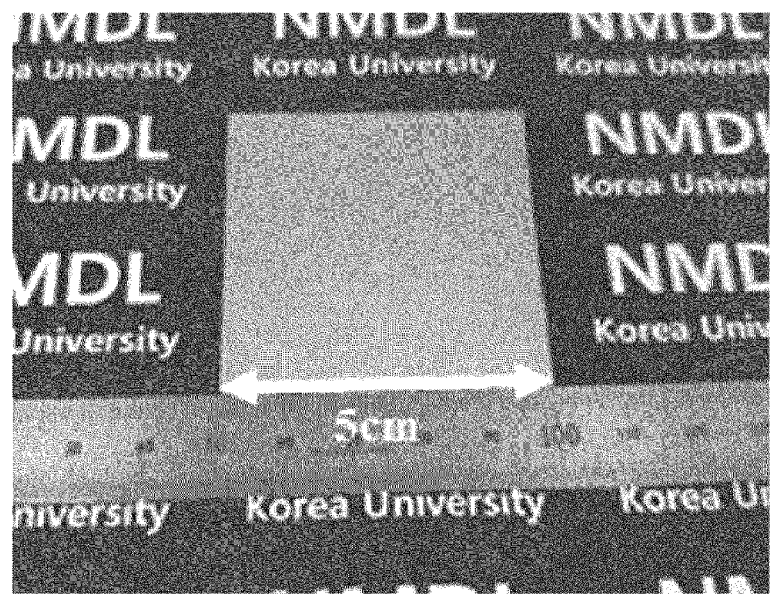
FIG. 26A is an image showing the appearance of a conventional radiative cooling device.
Figure 26B:
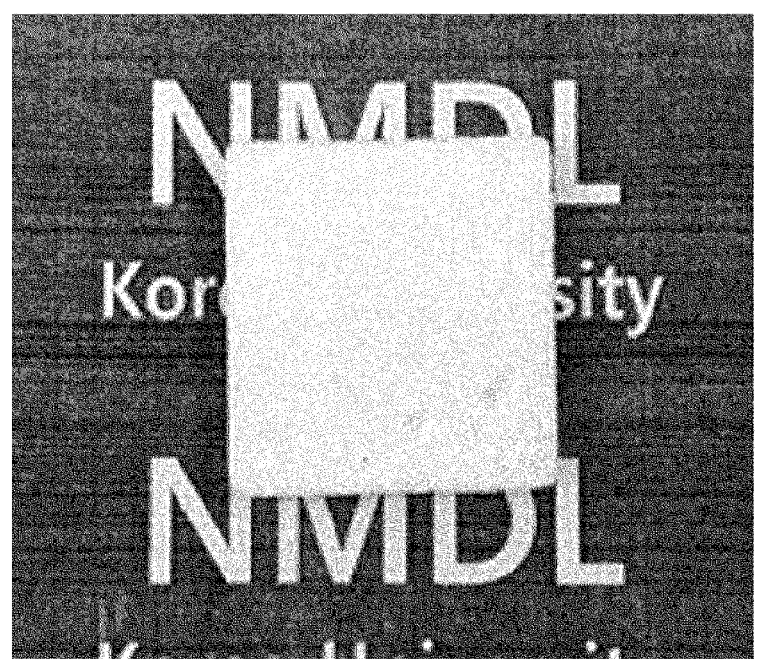
FIG. 26B is an image showing the appearance of a white radiative cooling device according to an embodiment of the present invention.

FIG. 26A is an image showing the appearance of a conventional radiative cooling device, and FIG. 26B is an image showing the appearance of a white radiative cooling device according to an embodiment of the present invention.

Referring to FIG. 26A, it can be confirmed that the conventional radiative cooling device in which a polymer layer is formed on a reflective layer has a metallic mirror-like color.

However, referring to FIG. 26B, it can be confirmed that the white radiative cooling device of Example 3 appears white.

Accordingly, it can be confirmed that, in the case of the white radiative cooling device of Example 2, since PUA particles reflect and scatter visible light, the white radiative cooling device appears white.

Figure 27:
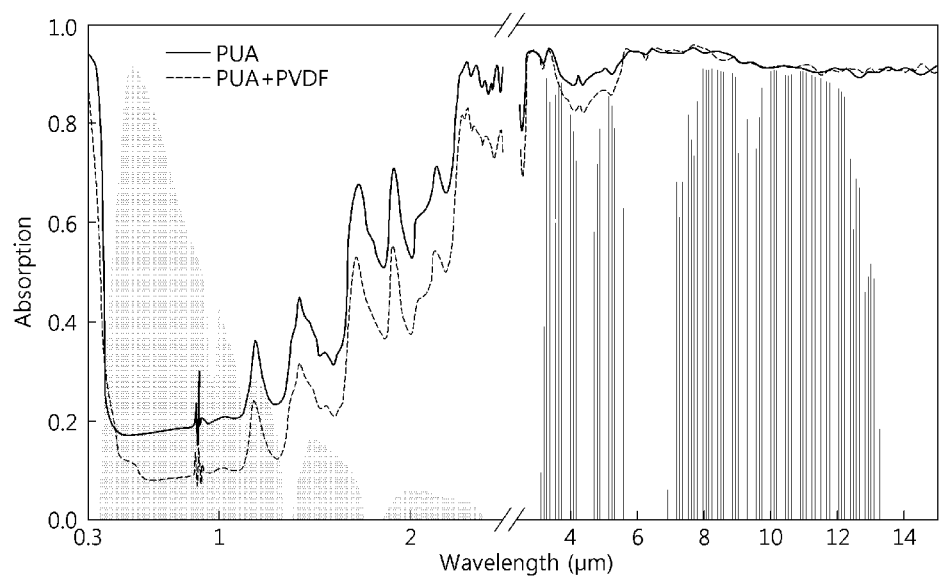
FIG. 27 is a graph showing the absorptivity of a white radiative cooling device according to the types of polymers included in a white radiative cooling layer according to an embodiment of the present invention.

FIG. 27 is a graph showing the absorptivity of the white radiative cooling device according to the types of polymers included in the white radiative cooling layer according to an embodiment of the present invention.

Referring to FIG. 27, it can be confirmed that Example 3 (PUA+PVDF) exhibits high reflectance with respect to visible light and exhibits high emissivity in a mid-infrared region.

In addition, as a result of observing the absorptivity of Example 3 (PUA+PVDF) and Comparative Example 2-1 (PUA) with respect to visible light, near-infrared light, and mid-infrared light, it can be seen that a cooling power efficiency of 35.42 W/m$^2$ is observed at an ambient temperature of 40° C.

In the yellow region corresponding to a visible region, the absorptivity of Example 3 is lower than that of Comparative Example 2-1. This result indicates that the visible light reflectance of Example 3 is higher than that of Comparative Example 2-1.

In addition, in the blue region corresponding to near-infrared and mid-infrared regions, Example 3 and Comparative Example 2-1 show almost similar emissivity. This results indicates that mid-infrared emissivity is not affected by the presence or absence of PUA particles.

In addition, in the white radiative cooling device including polymer fine particles according to an embodiment of the present invention, when the white radiative cooling device has the maximum emissivity in a mid-infrared region, even when the content of fine particles is further increased, the emissivity of the white radiative cooling device hardly changes.

Figure 28:
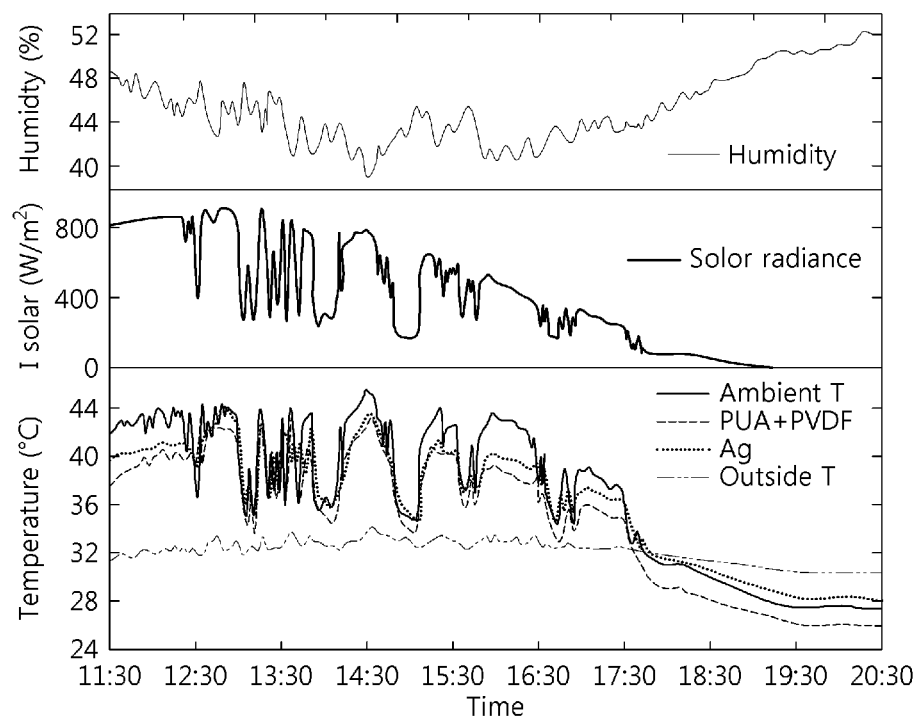
FIG. 28 is a graph showing the temperature of a white radiative cooling device including polymer fine particles according to an embodiment of the present invention over time.

FIG. 28 is a graph showing the temperature of a white radiative cooling device including polymer fine particles according to an embodiment of the present invention over time.

In this case, Ambient T shown in FIG. 28 is temperature inside of a chamber equipped with the radiative cooling device of Example 3 or Comparative Example 2-2, and is used to compare the degree of cooling of Example 3 and Comparative Example 2-2.

In addition, Outside T is temperature outside of the chamber and is lower than Ambient T due to convection.

Referring to FIG. 28, as a result of comparing changes in the temperature of Example 3 (PUA+PVDF) and atmospheric temperature (Ambient T), it can be confirmed that Example 3 is cooled by about 5.7° C. more than the atmospheric temperature.

In addition, when comparing the temperatures of Example 3 and Comparative Example 2-2, Example 3 is cooled by about 1.6° C. more than Comparative Example 2-2.

Accordingly, by including fine particles that reflect and scatter visible light and a polymer matrix that emits mid-infrared light, the white radiative cooling device according to an embodiment of the present invention may have excellent cooling performance compared to a conventional radiative cooling device.

Although the present invention has been described through limited examples and figures, the present invention is not intended to be limited to the examples. Those skilled in the art will appreciate that various modifications, additions, and substitutions are possible, without departing from the scope and spirit of the invention. Therefore, the scope of the present invention should not be limited by the embodiments, but should be determined by the following claims and equivalents to the following claims.

DESCRIPTION OF SYMBOLS 100, 200: RADIATIVE COOLING DEVICE
110, 210: SUBSTRATE
120, 220: REFLECTIVE LAYER
121: PIPE FOR HEAT EXCHANGE
130, 230: RADIATIVE COOLING LAYER
131: FIRST RADIATION LAYER
132: SECOND RADIATION LAYER
231: MID-INFRARED LIGHT ABSORPTION LAYER
232: FIRST COATING LAYER
233: SECOND COATING LAYER

The invention claimed is:

1. A radiative cooling device, comprising:
a reflective layer disposed on a substrate and responsible for reflecting sunlight having wavelengths corresponding to ultraviolet, visible, and near-infrared regions; and
a radiative cooling layer disposed on the reflective layer and responsible for absorbing sunlight having a wavelength corresponding to a mid-infrared region and emitting the sunlight as heat,
wherein the radiative cooling layer comprises a first radiation layer comprising an uneven pattern and a second radiation layer disposed on the first radiation layer and having a refractive index different from that of the first radiation layer,
wherein the radiative cooling layer comprises a mid-infrared light absorption layer disposed on the reflective layer and responsible for absorbing a first sunlight having a wavelength corresponding to a mid-infrared region and emitting the first sunlight as heat,
wherein a coating layer is disposed on the mid-infrared light absorption layer and comprises a first coating layer and a second coating layer having different refractive indexes with respect to a second sunlight having a wavelength corresponding to a visible region, and
wherein the first coating layer has a greater refractive index than the second coating layer with respect to the second sunlight and a difference between the refractive index of the first coating layer and the refractive index of the second coating layer is 0.7 to 2.

2. The radiative cooling device according to claim 1, wherein, in the radiative cooling layer, the first radiation layer and the second radiation layer are repeatedly disposed.

3. The radiative cooling device according to claim 1, wherein the reflective layer comprises at least one of silver (Ag), aluminum (Al), and platinum (Pt).

4. The radiative cooling device according to claim 1, wherein each of the first radiation layer and the second radiation layer comprises at least one of: fine particles made of an oxide or a nitride; a polymer; and a mixture of the fine particles and the polymer,
wherein the fine particles have a diameter of 10 nm to 20 µm,
wherein the fine particles comprise at least one of silica ($SiO_2$), zirconium oxide ($ZrO_2$), alumina ($Al_2O_3$), titanium dioxide ($TiO_2$), and silicon nitride ($Si_3N_4$), and
wherein the polymer is polydimethylsiloxane (PDMS) or dipentaerythritol penta/hexa acrylate (DPHA).

5. The radiative cooling device according to claim 1, wherein each of the first radiation layer and the second radiation layer has a thickness of 10 nm to 2,000 nm.

6. The radiative cooling device according to claim 1, wherein the coating layer reflects the second sunlight, the first coating layer and the second coating layer are repeatedly disposed in the coating layer.

7. The radiative cooling device according to claim 1, wherein the first coating layer comprises at least one of ZnS, Si, and Ge, and the second coating layer comprises $CaF_2$.

8. A method of manufacturing a radiative cooling device, the method comprising:
forming a reflective layer for reflecting sunlight having wavelengths corresponding to ultraviolet, visible, and near-infrared regions on a substrate; and
forming, on the reflective layer, a radiative cooling layer for absorbing sunlight having a wavelength corresponding to a mid-infrared region and emitting the sunlight as heat,
wherein forming the radiative cooling layer comprises forming, on the reflective layer, a first radiation layer comprising an uneven pattern and
forming, on the first radiation layer, a second radiation layer having a refractive index different from that of the first radiation layer,
wherein the radiative cooling layer comprises a mid-infrared light absorption layer disposed on the reflective layer and responsible for absorbing a first sunlight having a wavelength corresponding to a mid-infrared region and emitting the first sunlight as heat,
wherein a coating layer is disposed on the mid-infrared light absorption layer and comprises a first coating layer and a second coating layer having different refractive indexes with respect to a second sunlight having a wavelength corresponding to a visible region, and
wherein the first coating layer has a greater refractive index than the second coating layer with respect to the second sunlight and a difference between the refractive index of the first coating layer and the refractive index of the second coating layer is 0.7 to 2.

9. The method according to claim 8, wherein the first radiation layer is formed to have an uneven pattern using a stamp after the reflective layer is coated with at least one of: fine particles made of an oxide or a nitride; a polymer; and a mixture of the fine particles and the polymer.

10. The method according to claim 8, wherein the second radiation layer is formed by spin-coating at least one of: fine particles made of an oxide or a nitride; a polymer; and a mixture of the fine particles and the polymer on the substrate for 30 to 40 seconds.

11. The method according to claim 8, wherein forming the radiative cooling layer comprises:
forming, on the reflective layer, the mid-infrared light absorption layer; and
forming, on the mid-infrared light absorption layer, the coating layer,
wherein, in the forming the coating layer, the first coating layer and the second coating layer are formed on the mid-infrared light absorption layer.

12. A white radiative cooling device, comprising:
a substrate; and
a white radiative cooling layer disposed on the substrate, wherein, in the white radiative cooling layer, fine particles comprising a metal oxide or a polymer that reflects and scatters a first sunlight having a wavelength corresponding to a visible region are embedded in a polymer matrix that absorbs a second sunlight having a wavelength corresponding to a mid-infrared region and emits the second sunlight as heat,
wherein the white radiative cooling layer absorbs the second sunlight and emits the second sunlight as heat while reflecting and scattering the first sunlight, and wherein, in the white radiative cooling layer, fluorescent particles for emitting fluorescence are embedded in the polymer matrix.

13. The white radiative cooling device according to claim 12, wherein the white radiative cooling device becomes white due to reflection and scattering of first sunlight by the metal oxide-containing fine particles comprised in the white radiative cooling layer.

14. The white radiative cooling device according to claim 12, wherein the polymer matrix and the fine particles comprising the polymer have different refractive indexes, and
wherein the white radiative cooling device becomes white due to reflection and scattering of the first sunlight by the polymer containing fine particles comprised in the white radiative cooling layer.

15. The white radiative cooling device according to claim 12, wherein the polymer matrix comprises at least one of polydimethylsiloxane (PDMS), polymethyl methacrylate (PMMA), dipentaerythritol penta/hexa acrylate (DPHA), polyvinylidene fluoride (PVDF), and polyurethane acrylate (PUA).

16. The white radiative cooling device according to claim 12, wherein the metal oxide comprises at least one of titanium dioxide ($TiO_2$), zirconium oxide ($ZrO_2$), alumina ($Al_2O_3$), and zinc oxide (ZnO), and the polymer comprises at least one of polyvinylidene fluoride (PVDF) and polyurethane acrylate (PUA).

17. The white radiative cooling device according to claim 12, wherein the white radiative cooling device further comprises, on a lower surface of the white radiative cooling layer, a reflection enhancement layer for additionally reflecting the first sunlight, and
wherein the reflection enhancement layer comprises at least one of silver (Ag), aluminum (Al), and platinum (Pt).

18. The white radiative cooling device according to claim 17, wherein, in the white radiative cooling device, the reflection enhancement layer and the white radiative cooling layer are repeatedly disposed.

19. The white radiative cooling device according to claim 12, wherein, in the white radiative cooling layer, the fine particles are embedded in the polymer matrix.

* * * * *